(12) United States Patent
Libinaki

(10) Patent No.: US 10,071,030 B2
(45) Date of Patent: Sep. 11, 2018

(54) CARRIER COMPRISING NON-NEUTRALISED TOCOPHERYL PHOSPHATE

(75) Inventor: Roksan Libinaki, Clayton (AU)

(73) Assignee: Phosphagenics Limited, Victoria (AU)

( * ) Notice: Subject to any disclaimer, the term of this patent is extended or adjusted under 35 U.S.C. 154(b) by 0 days.

(21) Appl. No.: 13/577,124

(22) PCT Filed: Feb. 4, 2011

(86) PCT No.: PCT/AU2011/000112
§ 371 (c)(1),
(2), (4) Date: Aug. 3, 2012

(87) PCT Pub. No.: WO2011/094814
PCT Pub. Date: Aug. 11, 2011

(65) Prior Publication Data
US 2012/0321604 A1    Dec. 20, 2012

(30) Foreign Application Priority Data

Feb. 5, 2010 (AU) .................... 2010900463

(51) Int. Cl.
| | | |
|---|---|---|
| *A61K 8/23* | (2006.01) | |
| *A61K 8/34* | (2006.01) | |
| *A61K 8/36* | (2006.01) | |
| *A61K 8/67* | (2006.01) | |
| *A61K 8/92* | (2006.01) | |
| *A61Q 19/00* | (2006.01) | |
| *A23L 33/10* | (2016.01) | |
| *A23L 33/105* | (2016.01) | |
| *A23L 33/16* | (2016.01) | |

(52) U.S. Cl.
CPC ............ *A61K 8/23* (2013.01); *A23L 33/10* (2016.08); *A23L 33/105* (2016.08); *A23L 33/16* (2016.08); *A61K 8/347* (2013.01); *A61K 8/361* (2013.01); *A61K 8/678* (2013.01); *A61K 8/922* (2013.01); *A61Q 19/00* (2013.01); *A61K 2800/92* (2013.01)

(58) Field of Classification Search
USPC ....................................... 424/94.1
See application file for complete search history.

(56) References Cited

U.S. PATENT DOCUMENTS

| | | | |
|---|---|---|---|
| 2,407,823 A | 9/1946 | Fieser | |
| 2,457,932 A | 1/1949 | Solmssen et al. | |
| 2,667,479 A | 1/1954 | Hoffman et al. | |
| 2,913,477 A | 11/1959 | Hirschmann | |
| 3,127,434 A | 3/1964 | Andrews | |
| 3,212,901 A | 10/1965 | Robeson | |
| 3,607,765 A | 9/1971 | Wixon | |
| 4,075,333 A | 2/1978 | Josse | |
| 4,141,938 A | 2/1979 | Klose | |
| 4,299,906 A | 11/1981 | Liu | |
| 4,369,172 A | 1/1983 | Schor et al. | |
| 4,444,755 A | 4/1984 | Horrobin | |
| 4,603,142 A | 7/1986 | Burger et al. | |
| 4,654,373 A | 3/1987 | Bertelli | |
| 4,684,520 A | 8/1987 | Bertelli | |
| 4,686,211 A | 8/1987 | Hara et al. | |
| 4,874,883 A | 10/1989 | Uphues et al. | |
| 4,952,495 A | 8/1990 | Belly et al. | |
| 4,977,282 A | 12/1990 | Baldwin et al. | |
| 5,041,434 A | 8/1991 | Lubkin | |
| 5,053,222 A | 10/1991 | Takasu et al. | |
| 5,091,848 A | 2/1992 | Kojima | |
| 5,094,848 A | 3/1992 | Brixner | |
| 5,114,957 A | 5/1992 | Hendler et al. | |
| 5,138,084 A | 8/1992 | Casagrande et al. | |
| 5,173,304 A | 12/1992 | Lohner et al. | |
| 5,334,378 A | 8/1994 | Mitani et al. | |
| 5,374,645 A | 12/1994 | Kurihara-Bergstrom et al. | |
| 5,387,579 A | 2/1995 | Meybeck et al. | |
| 5,446,070 A | 8/1995 | Mantelle | |
| 5,474,891 A | 12/1995 | Murphy | |
| 5,474,991 A | 12/1995 | Ogata et al. | |
| 5,554,781 A | 9/1996 | Reierson | |
| 5,570,504 A | 11/1996 | Distefano et al. | |
| 5,583,105 A | 12/1996 | Kovacs et al. | |
| 5,589,504 A | 12/1996 | Dannenberg et al. | |
| 5,603,949 A | 2/1997 | Meybeck et al. | |
| 5,607,921 A | 3/1997 | Bernard et al. | |
| 5,643,597 A | 7/1997 | Meybeck et al. | |
| 5,656,618 A | 8/1997 | Meybeck et al. | |
| 5,656,672 A | 8/1997 | Collin et al. | |
| 5,741,518 A | 4/1998 | Ribier et al. | |
| 5,759,526 A | 6/1998 | Simonnet et al. | |
| 5,776,915 A | 7/1998 | Peterson et al. | |
| 5,780,504 A | 7/1998 | Ptchelintsev | |
| 5,804,168 A | 9/1998 | Murad | |
| 5,804,216 A | 9/1998 | Terren et al. | |
| 5,807,542 A | 9/1998 | Challis et al. | |
| 5,807,845 A | 9/1998 | Ogata et al. | |
| 5,885,595 A | 3/1999 | Corey et al. | |
| 5,906,811 A | 5/1999 | Hersh | |
| 5,908,846 A | 6/1999 | Bundgaard et al. | |
| 5,916,915 A | 6/1999 | Hong et al. | |
| 5,928,631 A | 7/1999 | Lucas et al. | |

(Continued)

FOREIGN PATENT DOCUMENTS

| | | |
|---|---|---|
| CA | 1337992 | 1/1996 |
| CA | 2426852 | 5/2002 |

(Continued)

OTHER PUBLICATIONS

Gianello et al. Alpha-tocopheryl phosphate: a novel, natural form of vitamin E. Free Radical Biology & Medicine. 2005;39:970-976.*

(Continued)

*Primary Examiner* — Lynn Y Fan
(74) *Attorney, Agent, or Firm* — Michael Best & Friedrich LLP

(57) ABSTRACT

The present invention relates to a carrier for the delivery of a nutraceutical or cosmeceutical active comprising non-neutralized tocopheryl phosphate and a hydrophobic vehicle. The present invention also relates to a formulation comprising the carrier and a nutraceutical or cosmeceutical active.

18 Claims, 4 Drawing Sheets

(56) References Cited

U.S. PATENT DOCUMENTS

| | | | |
|---|---|---|---|
| 5,952,361 A | 9/1999 | Dias Nahoum | |
| 5,952,373 A | 9/1999 | Lanzendorfer et al. | |
| 5,965,750 A | 10/1999 | Oonishi et al. | |
| 5,981,474 A | 11/1999 | Manning et al. | |
| 5,985,856 A | 11/1999 | Stella et al. | |
| 6,022,867 A | 2/2000 | Ito et al. | |
| 6,028,105 A | 2/2000 | Nigra | |
| 6,046,181 A | 4/2000 | Oonishi et al. | |
| 6,048,891 A | 4/2000 | Wechter | |
| 6,096,326 A | 8/2000 | Wikholm | |
| 6,121,249 A | 9/2000 | Weissman et al. | |
| 6,143,770 A | 11/2000 | Lane et al. | |
| 6,184,247 B1 | 2/2001 | Schneider | |
| 6,231,885 B1 | 5/2001 | Carrara | |
| 6,248,758 B1 | 6/2001 | Klokkers et al. | |
| 6,248,779 B1 | 6/2001 | Shimizu et al. | |
| 6,361,800 B1 | 3/2002 | Cooper et al. | |
| 6,384,043 B1 | 5/2002 | Peyman et al. | |
| 6,403,811 B1 | 6/2002 | West | |
| 6,417,223 B1 | 7/2002 | Sanders et al. | |
| 6,423,742 B1 | 7/2002 | Larson | |
| 6,444,220 B2 | 9/2002 | Wiley | |
| 6,444,234 B1 | 9/2002 | Kirby et al. | |
| 6,479,540 B1 | 11/2002 | Constantinides et al. | |
| 6,485,950 B1 | 11/2002 | Kumar et al. | |
| 6,503,545 B1 | 1/2003 | Perlman et al. | |
| 6,579,995 B1 | 6/2003 | West | |
| 6,599,933 B2 | 7/2003 | Takata et al. | |
| 6,641,847 B1 | 11/2003 | Nawar | |
| 6,645,998 B2 | 11/2003 | Sanders et al. | |
| 6,703,384 B2 | 3/2004 | Sanders et al. | |
| 6,727,280 B2 | 4/2004 | Paiepu et al. | |
| 6,770,672 B1 | 8/2004 | Sanders et al. | |
| 6,887,648 B2 | 5/2005 | Pavelchek et al. | |
| 7,074,825 B2 | 7/2006 | Mo et al. | |
| 7,179,486 B1 | 2/2007 | Mulye | |
| 7,648,710 B2 | 1/2010 | West | |
| 8,652,511 B2 | 2/2014 | Cottrell et al. | |
| 2001/0006659 A1 | 7/2001 | Koike et al. | |
| 2001/0044462 A1 | 11/2001 | Hensley et al. | |
| 2002/0045765 A1 | 4/2002 | Kim et al. | |
| 2002/0127198 A1 | 9/2002 | Rothbard et al. | |
| 2002/0131994 A1 | 9/2002 | Schur et al. | |
| 2002/0132845 A1 | 9/2002 | Miller et al. | |
| 2002/0151467 A1 | 10/2002 | Leung | |
| 2003/0035812 A1 | 2/2003 | Ito et al. | |
| 2003/0109575 A1 | 6/2003 | Lambert et al. | |
| 2003/0157326 A1 | 8/2003 | Vaghefi et al. | |
| 2003/0206972 A1 | 11/2003 | Babish et al. | |
| 2003/0220301 A1 | 11/2003 | Lal et al. | |
| 2004/0052745 A1 | 3/2004 | Bernard et al. | |
| 2004/0052754 A1 | 3/2004 | West et al. | |
| 2004/0067890 A1 | 4/2004 | Gupta | |
| 2004/0097431 A1 | 5/2004 | Sanders et al. | |
| 2004/0097472 A1 | 5/2004 | West et al. | |
| 2004/0102385 A1 | 5/2004 | Ames et al. | |
| 2004/0131569 A1 | 7/2004 | Schneider et al. | |
| 2004/0167081 A1 | 8/2004 | Abbruzzese et al. | |
| 2004/0204343 A1 | 10/2004 | Fishman | |
| 2004/0234602 A1 | 11/2004 | Fischer et al. | |
| 2004/0235938 A1 | 11/2004 | Sanders et al. | |
| 2004/0241225 A1 | 12/2004 | West | |
| 2004/0253318 A1 | 12/2004 | West et al. | |
| 2005/0009787 A1 | 1/2005 | West et al. | |
| 2005/0089495 A1 | 4/2005 | West | |
| 2005/0134664 A1 | 6/2005 | Pavlin | |
| 2005/0142174 A1 | 6/2005 | Assmus et al. | |
| 2005/0220733 A1 | 10/2005 | Tsuzuki et al. | |
| 2006/0120979 A1 | 6/2006 | Rubin | |
| 2006/0228395 A1 | 10/2006 | Lamb et al. | |
| 2006/0241085 A1 | 10/2006 | West et al. | |
| 2006/0257459 A1 | 11/2006 | West et al. | |
| 2006/0281715 A1 | 12/2006 | West | |
| 2006/0281716 A1 | 12/2006 | West et al. | |
| 2007/0042999 A1 | 2/2007 | West et al. | |
| 2007/0110739 A1 | 5/2007 | Logsdon | |
| 2007/0135390 A1 | 6/2007 | West et al. | |
| 2007/0141133 A1 | 6/2007 | Wang et al. | |
| 2007/0224253 A1 | 9/2007 | Franklin | |
| 2008/0233178 A1 | 9/2008 | Reidenberg et al. | |
| 2008/0254073 A1 | 10/2008 | Chi | |
| 2008/0299100 A1 | 12/2008 | Hsia et al. | |
| 2009/0004166 A1* | 1/2009 | West et al. | 424/94.1 |
| 2009/0005348 A1* | 1/2009 | Ogru et al. | 514/100 |
| 2009/0036354 A1* | 2/2009 | Gavin et al. | 514/3 |
| 2009/0104258 A1* | 4/2009 | Dumas et al. | 424/450 |
| 2009/0186856 A1 | 7/2009 | West et al. | |
| 2009/0233881 A1 | 9/2009 | West et al. | |
| 2009/0239827 A1 | 9/2009 | Ogru et al. | |
| 2009/0274677 A1* | 11/2009 | Isaacs et al. | 424/94.1 |
| 2009/0319191 A1 | 12/2009 | Rivas et al. | |
| 2009/0325953 A1 | 12/2009 | Sahoo et al. | |
| 2009/0325974 A1 | 12/2009 | Eggenweiler et al. | |
| 2010/0076094 A1 | 3/2010 | West et al. | |
| 2010/0209459 A1 | 8/2010 | West et al. | |
| 2010/0222305 A1 | 9/2010 | West et al. | |
| 2010/0261670 A1 | 10/2010 | West et al. | |
| 2011/0003774 A1 | 1/2011 | West et al. | |
| 2012/0202780 A1 | 8/2012 | Gavin et al. | |
| 2012/0283233 A1 | 11/2012 | Gavin et al. | |
| 2014/0255509 A1 | 9/2014 | Libinaki et al. | |
| 2015/0148431 A1 | 5/2015 | Cottrell et al. | |
| 2016/0184436 A1 | 6/2016 | Cottrell et al. | |
| 2017/0112863 A1 | 4/2017 | Libinaki et al. | |

FOREIGN PATENT DOCUMENTS

| | | |
|---|---|---|
| CA | 2426885 | 5/2002 |
| CN | 1600297 | 3/2005 |
| CN | 102079756 | 9/2012 |
| EP | 0171009 | 2/1986 |
| EP | 0324387 | 7/1989 |
| EP | 0338429 | 10/1989 |
| EP | 0430045 | 6/1991 |
| EP | 0430336 | 6/1991 |
| EP | 0436911 | 7/1991 |
| EP | 0565007 | 10/1993 |
| EP | 0574255 | 12/1993 |
| EP | 0612521 | 8/1994 |
| EP | 0617963 | 10/1994 |
| EP | 0641790 | 3/1995 |
| EP | 0643969 | 3/1995 |
| EP | 0650721 | 5/1995 |
| EP | 0661053 | 7/1995 |
| EP | 0669132 | 8/1995 |
| EP | 0669437 | 8/1995 |
| EP | 0674904 | 10/1995 |
| EP | 0679399 | 11/1995 |
| EP | 0680760 | 11/1995 |
| EP | 0681840 | 11/1995 |
| EP | 0684043 | 12/1995 |
| EP | 0699440 | 3/1996 |
| EP | 0826365 | 3/1998 |
| EP | 0845216 | 6/1998 |
| EP | 0699437 | 12/1998 |
| EP | 0965328 | 12/1999 |
| EP | 1000541 | 5/2000 |
| EP | 1023897 | 8/2000 |
| EP | 1053749 | 11/2000 |
| EP | 1264595 | 12/2002 |
| EP | 1470817 | 10/2004 |
| EP | 1783209 | 5/2007 |
| FR | 2777179 | 10/1999 |
| GB | 778142 | 7/1957 |
| GB | 1121683 | 7/1968 |
| GB | 2227662 | 8/1990 |
| JP | 50022535 | 3/1975 |
| JP | 52039013 | 3/1977 |
| JP | 53015381 | 2/1978 |
| JP | 58180410 | 10/1983 |
| JP | 59044375 | 3/1984 |
| JP | 59157091 | 9/1984 |
| JP | 60197621 | 10/1985 |
| JP | 61086940 | 5/1986 |

(56) References Cited

FOREIGN PATENT DOCUMENTS

| | | |
|---|---|---|
| JP | 61091137 | 5/1986 |
| JP | 61176535 | 8/1986 |
| JP | 61233631 | 10/1986 |
| JP | 62195393 | 8/1987 |
| JP | 63093791 | 4/1988 |
| JP | 63139972 | 6/1988 |
| JP | 1228920 | 9/1989 |
| JP | 1274830 | 11/1989 |
| JP | 03-072426 | 3/1991 |
| JP | 03-120230 | 5/1991 |
| JP | 4208209 | 7/1992 |
| JP | 4270212 | 9/1992 |
| JP | 05-000946 | 1/1993 |
| JP | 5132700 | 5/1993 |
| JP | 5201858 | 8/1993 |
| JP | 6048962 | 2/1994 |
| JP | 6056699 | 3/1994 |
| JP | 6078214 | 10/1994 |
| JP | 7011291 | 1/1995 |
| JP | 7207298 | 8/1995 |
| JP | 7278587 | 10/1995 |
| JP | 7316170 | 12/1995 |
| JP | 8073338 | 3/1996 |
| JP | 8193089 | 7/1996 |
| JP | 08-231564 | 9/1996 |
| JP | 8311085 | 11/1996 |
| JP | 8311489 | 11/1996 |
| JP | 8325594 | 12/1996 |
| JP | 9044375 | 2/1997 |
| JP | 9309813 | 12/1997 |
| JP | 10045783 | 2/1998 |
| JP | 10155429 | 6/1998 |
| JP | 10509451 | 9/1998 |
| JP | 10511677 | 11/1998 |
| JP | 11043436 | 2/1999 |
| JP | 11506419 | 6/1999 |
| JP | 11199424 | 7/1999 |
| JP | 11199465 | 7/1999 |
| JP | 2000198701 | 7/2000 |
| JP | 2001169731 | 6/2001 |
| JP | 2001247585 | 9/2001 |
| JP | 2002080475 | 3/2002 |
| JP | 2002088091 | 3/2002 |
| JP | 2003128531 | 5/2003 |
| JP | 2003171313 | 6/2003 |
| JP | 2006-143660 | 6/2008 |
| NZ | 244549 | 7/1994 |
| RU | 2296743 | 4/2007 |
| RU | 2302857 | 7/2007 |
| RU | 2373957 | 11/2009 |
| SU | 925961 | 5/1982 |
| UA | 29476 | 11/2000 |
| WO | WO 91/17987 | 11/1991 |
| WO | WO 92/03122 | 3/1992 |
| WO | WO 92/07544 | 5/1992 |
| WO | WO 92/08459 | 5/1992 |
| WO | WO 92/15289 | 9/1992 |
| WO | WO 93/02661 | 2/1993 |
| WO | WO 93/09768 | 5/1993 |
| WO | WO 93/15731 | 8/1993 |
| WO | WO 93/24131 | 12/1993 |
| WO | WO 95/31217 | 11/1995 |
| WO | WO 95/34303 | 12/1995 |
| WO | WO 96/17852 | 6/1996 |
| WO | WO 96/20715 | 7/1996 |
| WO | WO 96/21440 | 7/1996 |
| WO | WO 96/29336 | 9/1996 |
| WO | WO 96/37196 | 11/1996 |
| WO | WO 97/02803 | 1/1997 |
| WO | WO 97/14705 | 4/1997 |
| WO | WO 97/35591 | 10/1997 |
| WO | WO 99/35242 | 7/1999 |
| WO | WO 99/58555 | 11/1999 |
| WO | WO 00/08033 | 2/2000 |
| WO | WO 00/16772 | 3/2000 |
| WO | WO 00/30620 | 6/2000 |
| WO | WO 00/43380 | 7/2000 |
| WO | WO 00/44237 | 8/2000 |
| WO | WO 00/44375 | 8/2000 |
| WO | WO 00/53728 | 9/2000 |
| WO | WO 00/57876 | 10/2000 |
| WO | WO 00/59475 | 10/2000 |
| WO | WO 00/69865 | 11/2000 |
| WO | WO 00/71094 | 11/2000 |
| WO | WO 00/71125 | 11/2000 |
| WO | WO 00/74684 | 12/2000 |
| WO | WO 01/13901 | 3/2001 |
| WO | WO 01/19372 | 3/2001 |
| WO | WO 01/22937 | 4/2001 |
| WO | 01/35883 | 5/2001 |
| WO | WO 01/35998 | 5/2001 |
| WO | WO 01/46204 | 6/2001 |
| WO | WO 01/54674 | 8/2001 |
| WO | WO 01/58889 | 8/2001 |
| WO | WO 01/072300 | 10/2001 |
| WO | 02/02385 | 1/2002 |
| WO | WO 02/13810 | 2/2002 |
| WO | WO 02/26238 | 4/2002 |
| WO | WO 02/36736 | 5/2002 |
| WO | WO 02/39996 | 5/2002 |
| WO | WO 02/40033 | 5/2002 |
| WO | WO 02/40034 | 5/2002 |
| WO | 2002/096217 | 12/2002 |
| WO | WO 03/011303 | 2/2003 |
| WO | WO 03/013550 | 2/2003 |
| WO | WO 03/024429 | 3/2003 |
| WO | WO 03/024430 | 3/2003 |
| WO | WO 03/026673 | 4/2003 |
| WO | WO 03/039461 | 5/2003 |
| WO | WO 03/043570 | 5/2003 |
| WO | WO 03/049774 | 6/2003 |
| WO | WO 03/053407 | 7/2003 |
| WO | WO 03/068209 | 8/2003 |
| WO | WO 03/097714 | 11/2003 |
| WO | WO 03/101480 | 12/2003 |
| WO | WO 2004/014432 | 2/2004 |
| WO | WO 2004/060315 | 7/2004 |
| WO | WO 2004/064831 | 8/2004 |
| WO | WO 2004/091636 | 10/2004 |
| WO | WO 2004/092186 | 10/2004 |
| WO | WO 2004/092187 | 10/2004 |
| WO | WO 2005/023282 | 3/2005 |
| WO | WO 2005/084678 | 9/2005 |
| WO | WO 2006/012692 | 2/2006 |
| WO | 2006041506 | 4/2006 |
| WO | WO 2006/092024 | 9/2006 |
| WO | WO 2006/092025 | 9/2006 |
| WO | WO 2006/133506 | 12/2006 |
| WO | WO 2007/070981 | 6/2007 |
| WO | WO 2007/075883 | 7/2007 |
| WO | WO 2008/034178 | 3/2008 |
| WO | WO 2009/146443 | 12/2009 |
| WO | 2011/094814 | 8/2011 |
| WO | 2013/066400 | 5/2013 |

OTHER PUBLICATIONS

Reference. What are normal pH levels for the human stomach. Reference. 2016;1-5.*
International Search Report and Written Opinion for Application No. PCT/AU2011/000112 dated Feb. 25, 2011 (8 pages).
International Preliminary Report on Patentability for Application No. PCT/AU2011/000112 dated Jun. 6, 2012 (15 pages).
Aberg, F. et al., "Distribution and redox state of ubiquinones in rat and human tissues," Arch. Biochem. Biophys. (1992) 295(2):230-234.
Almeida, M.E.M. et al., "Evaluation of soybean oil deodorization distillate for Vitamin E recovery," Arq. Biol. Tecnol. (1994) 37(4):1003-1011.
Anslyn, E.V. et al., Modern Physical Organic Chemistry. Chapter 3: Solutions and Non-Covalent Binding Forces. University Science Books. (2006) see p. 146.

(56) References Cited

OTHER PUBLICATIONS

Barrett, C.W. et al., "The effect of particle size and vehicle on the percutaneous absorption of fluocinolone acetonide," Brit. J. Dermatol. (1965) 77:576-578.

Bikerman, J.J., "Mechanical destruction of young and old foam films," J. Phys. Chem. (1952) 56:164-165.

Block, L.H., "Chapter 44: Medicated Topicals," in Remington: The Science and Practice of Pharmacy, 20th edition, Edited by Alfonso R. Gennaro, Baltimore, MD, Lippincott, Williams & Wilkins (2000) 836-857.

Blom, J.H. et al., "Reproductive success of female rainbow trout (Oncorhynchus mykiss) in response to graded dietary ascorbyl monophosphate levels," Biol. of Reproduction (1995) 52:1073-1080.

Blum, A. et al., "Clinical and inflammatory effects of dietary L-arginine in patients with intractable angina pectoris," Amer. J. Cardiol. (1999) 1488-1489.

Brandt, M., "Steroid hormone biosynthesis," (2002) printed from http://www.rose_hulman.edu/~brandt/Chem430/Steroids.pdf on Nov. 20, 2010 (7 pages).

Cevc, G. "Transdermal drug delivery of insulin with ultradeformable carriers," Clin. Pharmacokinet. (2003) 42(5):461-474.

Cevc, G. et al., "Ultraflexible vesicles, transfersomes, have an extremely low pore penetration resistance and transport therapeutic amounts of insulin across the intact mammalian skin," Biochim. Biophys. Acta (1998) 1368:201-215.

De Wolfe, F.A. et al., "Ligand-binding proteins: their potential for application in systems for controlled delivery and uptake of ligands," Pharmacol. Rev. (2000) 52(2):207-236.

Devaraj, S. et la., "Alpha tocopherol decreases CD36 expression in human monocyte-derived macrophages," J. Lipid Res. (2001) 42:521-527.

Devaraj, S. et al., "Modulation of monocyte-macrophage function with alpha-tocopherol: implications for atherosclerosis," Nat. Rev. (2002) 60(1):8-14.

Devaraj, S. et al., "Alpha tocopherol supplementation decreases serum C-reactive protein and monocyte interleukin-6 levels in normal volunteers and type 2 diabetic patients," Free Radic. Biol. Med. (2000) 29(8):790-792.

Ernster, L. et al., "Biochemical, physiological and medical aspects of ubiquinone function," Biochim. Biophys. Acta (1995) 1271:195-204.

Fracalossi, D.M. et al., "Oscars, Astronotus ocellatus, have a dietary requirement for vitamin C," J. Nutrition (1998) 128:1745-1751.

Frei, B. et al., "Ubiquinol-10 is an effective lipid-soluble antioxidant at physiological concentrations," Proc. Natl. Acad. Sci. (1990) 87:4879-4883.

Gann, P.H. et al., "Lower prostate cancer risk in men with elevated plasma lycopene levels: results of a prospective analysis," Cancer Res. (1999) 59(6):1225-1230.

Gianello, R. et al., "α-tocopheryl phosphate: a novel, natural form of vitamin E," Free Radical Biol. Med. (2005) 39:970-976.

Gianello, R. et al., "Subchronic oral toxicity study of mixed tocopheryl phosphates in rats," Int'l J. Toxicol. (2007) 26:475-490.

Godin, B. et al., "Ethosomes: new prospects in transdermal delivery," Crit. Rev. Thera. Drug Car. Syst. (2003) 20(1):63-102.

Goff et al., "Prevention of cardiovascular disease in persons with Type 2 diabetes mellitus: current knowledge and rationale for the action to control cardiovascular risk in diabetes (ACCORD) trial," Am. J. Cardiol. (2007) 99(suppl):4i-20i.

Griffin, E. et al., "A link between diabetes and atherosclerosis: glucose regulates expression of CD36 at the level of translation," Nature Med. (2001) 7(7):840-846.

Guo, J. et al., "Transdermal delivery of insulin in mice by using Lecithin vesicles as a carrier," Drug Del. (2000) 7:113-116.

Guthrie et al., "VIIth Asian Conference of Nutrition: Lipid Symposium Proceedings," Journal of Nutrition, 1997, vol. 127, pp. 544s-548s.

Heron-Milhavet, L. et al., "Muscle-specific overexpression of CD36 reverses the insulin resistance and diabetes of MKR mice," Endocrinology (2004) 145:4667-4676.

Imada, I. et al., "Photochemical Reaction of Ubiquinone. IV. Coenzymatic activity of ubiquinone and related compounds," Chem. Pharm. Bull. (1965) 13:136-142.

Iimura, N. et al., "Complex formation between cationic surfactantsand insoluble drugs," Bull. Chem. Soc. Jpn. (1999) 72:2417-2422.

International Specialty Products,"A Product Guide. Performance enhancing Products for Pharmaceuticals," (2005) 20 pages [retrieved on Jul. 27, 2010 from http://web.archieve.org/web/20060623233652/http://abstracts.aapspharmaceutica.com/ExpoAAPS06/Data/EC/Event/Exhibitors/309/4ecb9a3a-65d0-4c69-a762-c60e099922ee.pdf, published on Jun. 23, 2006 as per Wayback Machine].

Isoda, K. et al., "Metformin inhibits proinflammatory responses and nuclear factor-κB in human vascular wall cells," Arterioscler. Thromb. Vasc. Biol. (2006) 26:611-617.

Jiang, Q. et al., "γ-tocopherol induces apoptosis in androgen-responsive LNCaP prostate cancer cells via caspase-dependent and independent mechanisms," Annals of the New York Academy of Sciences, 2004, vol. 103, pp. 399-400.

Jiang, Q. et al., "γ-tocopherol, the major form of vitamin E in the U.S. diet, deserves more attention," Am. J. Clin. Nutri. (2001) 74(6):714-722.

Kagan, V. et al., "Antioxidant effects of ubiquinones in microsomes and mitochondria are mediated by tocopherol recycling," Biochem. Biophys. Res. Commun. (1990) 169(3):851-857.

Karrer, V.P. et al., "d,l-alpha-tocopherol-phosphorsaure-ester," Zurich, Chemisches Institut der Universitat (1933) p. 1137-1138, in German.

King, M.J. et al., "Transdermal delivery of insulin from a novel biphasic lipid system in diabetic rats," Diab. Tech. Therap. (2002) 4(4):479-488.

Knowler, W.C. et al., "Preventing Non-insulin-dependent diabetes," Diabetes (1995) 44:483-488.

Koh, "Antioxidants in a carotenoid-rich edible oil," Journal of Japan Mibyou System Association, 2003, vol. 9, No. 1, pp. 12-13.

Langsjoen, P.H. et al., "Overview of the use of CoQ10 in cardiovascular diseases," Biofactors (1999) 9:273-284.

Lass, A. et al., "Electron transport-linked ubiquinone-dependent recycling of α-tocopherol inhibits autooxidation of mitochondrial membranes," Arch. Biochem. Biophys. (1998) 352(2):229-236.

Lee, C-F. et al., "Attenuation of UV-induced apoptosis by coenzyme Q10 in human cells harboring large-scale deltion of mitochontrial DNA," Ann. N.Y. Acad. Sci. (2005) 1042:429-438.

Lei, B. et al.,. Progress in alpha-tocopherol preparation technology, Xiandai Huagong (1997) 17(7):13-15.

Libinaki, R. et al., "Evaluation of the safety of mixed tocopheryl phosphates (MTP)—a formulation of α-tocopheryl phosphate plus α-di-tocopheryl phosphate," Food Chem. Toxicol. (2006) 44(7):916-932.

Little, P.J. et al., "Phosphorylated troglitazone activates PPARγ and inhibits vascular smooth muscle cell proliferation and proteoglycan synthesis," J. Cardiovasc. Pharmacol. (2008) 51(3):274-279.

Maguire, J.J. et al., "Succinate-ubiquinone reductase linked recycling of alpha-tocopherol in reconstituted systems and mitochondria: requirement for reduced ubiquinone," Arch. Biochem. Biophys. (1992) 292(1):47-53.

Mellors, A. et al., "The inhibition of mitochondrial peroxidation by ubiquinone and ubiquinol," J. Biol. Chem. (1966) 241(19):4353-4356.

Merck Index, The, "α-estradiol" Thirteenth Edition, Whitehouse Station, NJ (2001) p. 660.

Merck Index, The, "Fludarabine to Fludeoxyglucose F18" pages, Thirteenth Edition, Whitehouse Station, NJ (2001) pp. 729-730.

Min, J. et al., "Effect of apoptosis induced by different vitamin E homologous analogues in human hepatoma cells (HepG2)," J. Hygiene Res. China (2003) 32(4):343-345.

Miyamoto, S. et al., "Synthesis of a novel phosphate ester of a vitamin E derivative and its antioxidative activity," Biosci. Biotech. Biochem. (1998) 62(12):2463-2466.

(56) References Cited

OTHER PUBLICATIONS

Morgan, T.M. et al., "Transdermal delivery of estradiol in postmenopausal women with a novel topical aerosol," J. Pharm. Sci. (1998) 87(10):1226-1228.
Morgan, T.M. et al., "Enhanced transdermal delivery of sex hormones in swine with a novel topical aerosol," J. Pharm. Sci. (1998) 87(10):1219-1225.
Mortensen, S.A., "Perspectives on therapy of cardiovascular diseases with coenzyme Q10 (ubiquinone)," Clin. Investig. (1993) 71(Suppl.8):S116-S123.
Mottu, F. et al., "Organic solvents for pharmaceutical parenterals and embolic liquids: a review of toxicity data," PDA Journal of Pharm. Sci. Tech. (2000) 54(6):456-469.
Mukherjee, S. et al., "Cardioprotection with α-tocopheryl phosphate: amelioration of myocardial ischemia reperfusion injury is linked with its ability to generate a survival signal through Akt activation," Biochim. Biophys. Acta (2008) 1782:498-503.
Munteanu, A. et al., "Modulation of cell proliferation and gene expression by alpha-tocopheryl phosphates: relevance to atherosclerosis and inflammation," Biochem. Biophys. Res. Comm. (2004) 318(1):311-316.
Nakayama, S. et al., "Protective effects of a stable, water-soluble vitamin E on photodamage induced by UVB irradiation in cultured mouse skin," Photomedicine and Photobiology (1998) 20:99-100.
Negis, Y. et al., "On the existence of cellular tocopheryl phosphate, its synthesis, degradation and cellular roles: a hypothesis," IUBMB Life (2005) 57(1):23-25.
Negis, Y. et al., "Molecular mechanism of alpha-tocopheryl-phospate transport across the cell membrane," Biochem. Biophys. Res. Comm. (2007) 359:348-353.
Negis, Y. et al., "The effect of tocopheryl phosphates on atherosclerosis progression in rabbits fed with a high cholesterol diet," Arch. Biochem. Biophys. (2006) 450:63-66.
Octoplus, "Formulation Development of Poorly Soluble Drugs" (www.octoplus.nl) (1999) 2 pages (downloaded Nov. 2008).
Ogru, E. et al., "Vitamin E phosphate: an endogenous form of vitamin E," Medimond S.r.l. (2003) 127-132.
Ostrenga, J. et al., "Significance of vehicle composition I: Relationship between topical vehicle composition, skin penetrability, and clinical efficacy," J. Pharm. Sci. (1971) 60(8):1175-1179.
Owens, D.R. et al., "Alternative routes of insulin delivery," Diabet. Med. (2003) 20:886-898.
Parker et al., "Neonatal vitamin K administration and childhood cancer in the North of England: retrospective case-control study," BMJ (1998) 316:189-193.
Pastori et al., "Lycopene in association with α-tocopherol inhibits at physiological concentrations proliferation of prostate carcinoma cells," Biochemical and Biophysical Research Communications, 1998, vol. 250, pp. 582-585.
Potts, R.O. et al., "Predicting skin permeability," Pharm. Res. (1992) 9(5):663-669.
Puratchikody, A. et al., "Reverse phase—high performance liquid chromatographic determination of atorvastatin calcium in solid dosage forms," Pharma. Review (2003) 1(2):79-80, 83—STN File CA, Abstract 139:399976 only.
Rerek, M.E. et al., "Disodium lauriminodipropionate tocopheryl phosphates: a potent new anti-inflammatory," Cosmetics & Toiletries magazine (2003) 118(7):63-67.
Rezk, B.M. et al., "The extraordinary antioxidant activity of vitamin E phosphate," Biochim. Biophys. Acta (2004) 1683:16-21.
Ricciarelli, R. et al., "Vitamin E reduces the uptake of oxidized LDL by inhibiting CD36 scavenger receptor expression in cultured aortic smooth muscle cells," Circulation (2000) 102:82-87.
Schwenke, D.C. et al., "α-tocopherol protects against diet induced atherosclerosis in New Zealand white rabbits," J. Lipid Res. (2002) 43:1927-1938.
Sevast'Ianov, V.I. et al., "Transdermal delivery of insulin," Meditsinskaia Tekhnika (2003) 2:21-24.

Seyama, Y. et al., "Comparative effects of Vitamin K2 and estradiol on experiemental arteriosclerosis with diabetes mellitus," Int. J. Vitam. Nutr. Res. (2000) 70(6):301-304, Abstract only.
Sharma H. et al., "An excerpt from the medical textbook Contemporary Ayurverda," Edinburgh: Churchill Livingston, 1998, 6 pages, Retrieved from Internet on Nov. 1, 2012 <URL: http://www.bsherman.net/freeradicals.htm>.
Singh, R.B. et al., "Randomized double-blind placebo-controlled trial of coenzyme Q10 in patients with acute myocardial infarction," Cardiov. Drugs Ther. (1998) 12:347-353.
Sinha, V.R. et al., "Coating polymers for colon specific drug delivery: A comparative in vitro evaluation," Acta. Pharm., 2003, vol. 53, pp. 41-47.
Stedman's Medical Dictionary, "Tocopherol," "Tocotrienol," and "Vitamin K1", 22nd Edition, Williams & Wilkins Co. (1972) p. 1303 and 1400.
Suzuki, T. et al., "The solution behavior and the association structure of long-chain monoalkyl phosphates," Chem. Soc. Japan (1986) 633-640, with English abstract.
Teupser, D. et al., "Alpha-tocopherol down-regulates scavenger receptor activity in macrophages," Atherosclerosis (1999) 144:109-115.
Traber, M.G. et al., "Human plasma vitamin E kinetics demonstrates rapid recycling of plasma RRR-alpha-tocophero," Proc. Natl. Acad. Sci. USA (1994) 91:10005-10008.
Visarius, T. et al., "Inhibition of human prostate cancer cell proliferation: vitamin E and lycopene targeted pathways regulating cell cycle progression," FASEB J. (2004) 18(8):C103.
Walters et al., "The effects of surfactants on penetration across the skin," Inter. J. Cosmetic Sci. (1993) 15:260-270.
Williams, A.C. et al., "Penetration enhancers," Advanced Drug Delivery Reviews (2004) 56(5):603-618.
Younis et al., "The prevention of type 2 diabetes mellitus: recent advances," Q.J. Med. (2004) 97:451-455.
United States Office Action for U.S. Appl. No. 09/979,436 dated Apr. 4, 2002 (6 pages).
United States Office Action for U.S. Appl. No. 09/979,436 dated Sep. 23, 2002 (6 pages).
United States Office Action for U.S. Appl. No. 10/416,775 dated Nov. 2, 2005 (10 pages).
United States Office Action for U.S. Appl. No. 10/416,775 dated Jun. 12, 2006 (10 pages).
United States Office Action for U.S. Appl. No. 10/416,775 dated Jul. 12, 2007 (11 pages).
United States Office Action for U.S. Appl. No. 10/416,775 dated Dec. 17, 2008 (6 pages).
United States Patent Office Action for U.S. Appl. No. 12/628,443 dated Feb. 18, 2011 (15 pages).
United States Patent Office Action for U.S. Appl. No. 12/628,443 dated Aug. 5, 2011 (8 pages).
United States Patent Office Notice of Allowance for U.S. Appl. No. 12/628,443 dated Jan. 12, 2012 (7 pages).
United States Office Action for U.S. Appl. No. 10/416,774 dated Sep. 6, 2007 (9 pages).
United States Office Action for U.S. Appl. No. 10/416,774 dated Jun. 11, 2008 (15 pages).
United States Office Action for U.S. Appl. No. 10/416,774 dated Feb. 17, 2009 (15 pages).
United States Office Action for U.S. Appl. No. 10/416,774 dated Apr. 15, 2009 (14 pages).
United States Patent Office Action for U.S. Appl. No. 10/416,774 dated Dec. 18, 2009 (11 pages).
United States Office Action for U.S. Appl. No. 10/462,480 dated Dec. 1, 2006 (10 pages).
United States Office Action for U.S. Appl. No. 10/462,480 dated Nov. 1, 2007 (10 pages).
United States Office Action for U.S. Appl. No. 10/462,480 dated Feb. 20, 2009 (17 pages).
United States Patent Office Action for U.S. Appl. No. 10/462,480 dated Nov. 27, 2009 (9 pages).
United States Patent Office Action for U.S. Appl. No. 12/768,307 dated Oct. 6, 2011 (13 pages).

(56) References Cited

OTHER PUBLICATIONS

United States Patent Office Action for U.S. Appl. No. 12/782,438 dated Aug. 30, 2012 (14 pages).
United States Office Action for U.S. Appl. No. 10/485,196 dated May 29, 2008 (23 pages).
United States Office Action for U.S. Appl. No. 10/485,196 dated Jul. 23, 2009 (9 pages).
United States Patent Office Action for U.S. Appl. No. 10/485,196 dated Jan. 25, 2010 (8 pages).
United States Patent Office Action for U.S. Appl. No. 10/485,196 dated Oct. 29, 2010 (13 pages).
United States Patent Office Notice of Allowance for U.S. Appl. No. 10/485,196 dated Apr. 14, 2011 (7 pages).
United States Office Action for U.S. Appl. No. 10/486,142 dated Mar. 18, 2008 (12 pages).
United States Patent Office Action for U.S. Appl. No. 12/212,803 dated Mar. 12, 2010 (13 pages).
United States Office Action for U.S. Appl. No. 10/487,743 dated Dec. 2, 2005 (22 pages).
United States Office Action for U.S. Appl. No. 10/487,743 dated Jul. 27, 2006 (23 pages).
United States Office Action for U.S. Appl. No. 10/498,684 dated Oct. 2, 2008 (21 pages).
United States Office Action for U.S. Appl. No. 10/498,684 dated Jun. 23, 2009 (19 pages).
United States Patent Office Action for U.S. Appl. No. 10/498,684 dated Jul. 7, 2010 (21 pages).
United States Office Action for U.S. Appl. No. 10/524,090 dated Mar. 12, 2008 (12 pages).
United States Patent Office Action for U.S. Appl. No. 10/524,090 dated Mar. 3, 2010 (18 pages).
United States Patent Office Action for U.S. Appl. No. 10/524,090 dated Nov. 23, 2010 (19 pages).
United States Office Action for U.S. Appl. No. 10/542,511 dated Aug. 8, 2007 (19 pages).
United States Office Action for U.S. Appl. No. 10/542,511 dated Mar. 31, 2008 (20 pages).
United States Office Action for U.S. Appl. No. 10/542,511 dated Feb. 5, 2009 (23 pages).
United States Patent Office Action for U.S. Appl. No. 10/542,511 dated Jan. 12, 2010 (13 pages).
United States Patent Office Advisory Action for U.S. Appl. No. 10/542,511 dated May 25, 2010 (3 pages).
United States Patent Office Action for U.S. Appl. No. 12/834,553 dated Apr. 14, 2011 (13 pages).
United States Patent Office Action for U.S. Appl. No. 12/834,553 dated Oct. 7, 2011 (11 pages).
United States Office Action for U.S. Appl. No. 10/551,200 dated Jan. 28, 2009 (11 pages).
United States Office Action for U.S. Appl. No. 10/551,201 dated Jan. 24, 2008 (6 pages).
United States Office Action for U.S. Appl. No. 10/551,203 dated Dec. 6, 2006 (13 pages).
United States Office Action for U.S. Appl. No. 10/551,203 dated Sep. 7, 2007 (13 pages).
United States Office Action for U.S. Appl. No. 10/551,203 dated Apr. 11, 2008 (11 pages).
United States Office Action for U.S. Appl. No. 10/551,203 dated Dec. 19, 2008 (13 pages).
United States Office Action for U.S. Appl. No. 10/551,203 dated Jul. 21, 2009 (21 pages).
United States Patent Office Action for U.S. Appl. No. 12/690,735 dated Sep. 27, 2011 (15 pages).
United States Patent Office Action for U.S. Appl. No. 12/690,735 dated Aug. 2, 2012 (9 pages).
United States Patent Office Action for U.S. Appl. No. 11/572,864 dated Mar. 15, 2012 (15 pages).
United States Patent Office Action for U.S. Appl. No. 11/572,864 dated Nov. 8, 2012 (16 pages).
United States Patent Office Action for U.S. Appl. No. 11/817,439 dated Nov. 24, 2010 (15 pages).
United States Patent Office Action for U.S. Appl. No. 11/817,439 dated May 11, 2011 (11 pages).
United States Patent Office Action for U.S. Appl. No. 11/817,439 dated Jul. 29, 2011 (2 pages).
United States Patent Office Action for U.S. Appl. No. 11/817,439 dated Nov. 7, 2012 (10 pages).
United States Patent Office Action for U.S. Appl. No. 11/817,453 dated Oct. 9, 2009 (11 pages).
United States Patent Office Action for U.S. Appl. No. 11/817,453 dated Aug. 2, 2010 (10 pages).
United States Patent Office Action for U.S. Appl. No. 11/817,453 dated Mar. 9, 2011 (12 pages).
United States Patent Office Action for U.S. Appl. No. 11/817,453 dated Oct. 13, 2011 (14 pages).
United States Patent Office Action for U.S. Appl. No. 11/917,831 dated Jan. 19, 2011 (10 pages).
United States Patent Office Action for U.S. Appl. No. 11/917,831 dated Oct. 24, 2011 (11 pages).
United States Patent Office Action for U.S. Appl. No. 12/158,932 dated Aug. 19, 2010 (15 pages).
United States Patent Office Action for U.S. Appl. No. 12/782,560 dated Sep. 1, 2011 (18 pages).
United States Patent Office Action for U.S. Appl. No. 12/782,560 dated May 24, 2012 (22 pages).
United States Patent Office Action for U.S. Appl. No. 12/782,564 dated Sep. 1, 2011 (20 pages).
United States Patent Office Action for U.S. Appl. No. 12/782,564 dated May 24, 2012 (25 pages).
United States Patent Office Action for U.S. Appl. No. 13/501,498 dated Nov. 21, 2014 (9 pages).
Zia et al., Pharmaceutical Research, vol. 8, No. 4, 1991.
United States Patent Office Final Rejection for U.S. Appl. No. 13/501,498 dated Apr. 8, 2015 (16 pages).
United States Patent Office Action for U.S. Appl. No. 14/004,973 dated Apr. 9, 2015 (12 pages).
United States Patent Office Final Rejection for U.S. Appl. No. 13/683,698 dated Jan. 29, 2015 (17 pages).
United States Patent Office Action for U.S. Appl. No. 14/550,514 dated Apr. 23, 2015 (13 pages).
Advantages of Liposomal Delivery Systems for Anthracyclines, Semin. Oncol., 2004, 6 Suppl 13, 5-15.
United States Patent Office Action for U.S. Appl. No. 11/917,831 dated Oct. 3, 2014 (9 pages).
Magnusson et al., "Terpenes and ethanol enhance the transdermal permeation of the tripeptide thyrotropin releasing hormone in human epidermis," International Journal of Pharmaceutics 157, 1997, 113-121.
United States Patent Office Action for U.S. Appl. No. 13/501,494 dated Nov. 18, 2014 (16 pages).
United States Patent Office Action for U.S. Appl. No. 13/501,494 dated Jan. 26, 2016 (20 pages).
United States Patent Office Action for U.S. Appl. No. 13/501,498 dated Dec. 4, 2015 (10 pages).
United States Patent Office Notice of Allowance for U.S. Appl. No. 14/550,514 dated Dec. 10, 2015 (6 pages).
United States Patent Office Action for U.S. Appl. No. 13/683,698 dated Sep. 1, 2015 (19 pages).
United States Patent Office Action for U.S. Appl. No. 14/004,973 dated Oct. 20, 2015 (14 pages).
United States Patent Office Notice of Allowance for U.S. Appl. No. 11/917,831 dated Jul. 8, 2015 (7 pages).
U.S. Appl. No. 15/218,719, filed Jul. 25, 2016, Gavin et al.
U.S. Appl. No. 15/261,455, filed Sep. 9, 2009, Gavin et al.
United States Patent Office Notice of Allowance for U.S. Appl. No. 14/004,973 dated Sep. 28, 2016 (5 pages).
Saikinnno (1991) 149-155, 195-198.
Saishinn (1984) 137-147, 190-201.
United States Patent Office Action for U.S. Appl. No. 13/501,498 dated Jun. 9, 2016 (14 pages).
United States Patent Office Action for U.S. Appl. No. 14/004,973 dated Apr. 13, 2016 (13 pages).

(56) References Cited

OTHER PUBLICATIONS

United States Patent Office Action for U.S. Appl. No. 15/065,510 dated Dec. 12, 2016 (14 pages).
United States Patent Office Action for U.S. Appl. No. 15/261,455 dated Feb. 27, 2017 (12 pages).
Munteanu et al., "Modulation of cell proliferation and gene expression by—tocopheryl phosphates: relevance to atherosclerosis and inflamation" Biochemical and Biophysical Research Communications, 2004, vol. 318, pp. 311-316.
Rosenson et al., "Hypertriglyceridemia is associated with an elevated blood viscosity Rosenson: triglycerides and blood viscosity", Atherosclerosis, 2002, vol. 161, Issue 2, pp. 433-439.
United States Patent Office Action for U.S. Appl. No. 11/817,453 dated Feb. 21, 2014 (13 pages).
United States Patent Office Action for U.S. Appl. No. 13/501,494 dated Apr. 21, 2014 (19 pages).
Madhavi et al., "Enhanced transdermal drug penetration of curcumin via ethosomes," Malaysian Journal of Pharmaceutical Sciences (2013) 11(1):49-58.
Dolfi, S. C. et al., "Inhibitory Effects of Different Forms of Tocopherols, Tocopherol Phosphates, and Tocopherol Quinones on Growth of Colon Cancer Cells," Journal of Agricultural and Food Chemistry, 2013, vol. 61, No. 36, pp. 8533-8540.
International Search Report for Application No. PCT/AU2017/051381 dated Feb. 13, 2018 (7 pages).
International Search Report for Application No. PCT/AU2017/051363 dated Jan. 25, 2018(8 pages).
United States Patent Office Action for U.S. Appl. No. 15/400,356 dated Feb. 22, 2018 (12 pages).
United States Patent Office Action for U.S. Appl. No. 15/261,455 dated Mar. 22, 2018 (6 pages).
United States Patent Office Action for U.S. Appl. No. 11/572,864 dated Sep. 16, 2013 (10 pages).
United States Patent Office Final Rejection for U.S. Appl. No. 13/501,494 dated Aug. 22, 2013 (13 pages).
United States Patent Office Action for U.S. Appl. No. 13/501,499 dated Sep. 25, 2013 (12 pages).
Li et al ("Effect of HPMC and Carbopol on the release and floating properties of gastric floating drug delivery system using factorial design." International Journal of Pharmaceutics, 2003; 253:13-22.).
Barry ("Novel mechanisms and devices to enable successful transdermal drug delivery." Sciences, 2001; 14:101-114).
United States Patent Office Notice of Allowance for U.S. Appl. No. 13/501,500 dated Aug. 21, 2013 (11 pages).
United States Patent Office Action for U.S. Appl. No. 13/501,498 dated Feb. 21, 2013 (12 pages).
Maugard et al., "Synthesis of Water-Soluble Retinol Derivatives by Enzymatic Method," Biotechnol. Prog., 2002, vol. 18, pp. 424-428.
United States Patent Office Action for U.S. Appl. No. 13/683,698 dated Apr. 24, 2013 (18 pages).
United States Patent Office Action for U.S. Appl. No. 13/501,494 dated Dec. 18, 2012 (13 pages).
United States Patent Office Action for U.S. Appl. No. 13/501,500 dated Dec. 17, 2012 (14 pages).
United States Patent Office Action for U.S. Appl. No. 13/683,698 dated Jun. 20, 2014 (17 pages).
United States Patent Office Action for U.S. Appl. No. 11/572,864 dated Jun. 20, 2014 (11 pages).
United States Patent Office Action for U.S. Appl. No. 14/086,738 dated May 22, 2014 (14 pages).
Gavin, P. et al., "Transdermal delivery of various molecules in vivo using alpha-tocopheryl phosphate," Drug Delivery Technology (2008) 8(9):34-41.
United States Patent Office Final Rejection for U.S. Appl. No. 13/501,498 dated Nov. 14, 2013 (10 pages).
United States Patent Office Final Rejection for U.S. Appl. No. 13/683,698 dated Nov. 14, 2013 (15 pages).
Squillante et al, European Journal of Pharmaceutics and Biopharmaceutics 46 (1998) 265-271.
Chae, B. J. et al. 'Effects of incremental levels of alpha-tocopherol acetate on performance, nutrient digestibility and meat quality of commercial broilers', Asian Australasian Journal of Animal Sciences. 2006, vol. 19, No. 2, pp. 203-208.
Ghayour-Mobarhan, M. et al., 'α-Tocopheryl Phosphate as a Bioactive Derivative of Vitamin E: A Review of the Literature', Journal of Dietary Supplements. 2014, vol. 12, No. 4, pp. 359-372.
Zingg, J.-M. et al., 'α-Tocopheryl phosphate—An active lipid mediator?', Molecular Nutrition and Food Research. 2010, vol. 54, pp. 679-692.
United States Patent Office Action for U.S. Appl. No. 15/218,719 dated Sep. 25, 2017 (12 pages).
Trommer et al., "Overcoming the Stratum Corneum: The Modulation of Skin Penetration," Skin Pharmacol Physiol, 2006, 19:106-121.
United States Patent Office Action for U.S. Appl. No. 15/261,455 dated Sep. 6, 2017 (10 pages).
United States Patent Office Action for U.S. Appl. No. 15/400,356 dated Oct. 19, 2017 (12 pages).

\* cited by examiner

CARRIER COMPRISING NON-NEUTRALISED TOCOPHERYL PHOSPHATE

CROSS-REFERENCE TO RELATED APPLICATIONS

This patent application is a national stage filing under 35 U.S.C. § 371 of International Application No. PCT/AU2011/000112, filed on 4 Feb. 2011, which claims foreign priority to Australian Patent Application No. 2010900463, filed on 5 Feb. 2010. Priority to each application is hereby claimed.

TECHNICAL FIELD

The invention relates to a carrier for the delivery of nutraceutical and cosmeceutical actives comprising a hydrophobic vehicle. The carrier of the present invention is suitable for enteral or parenteral administration of the nutraceutical and cosmeceutical actives.

BACKGROUND

Nutrients that we require every day to remain healthy and active are provided by our diet. This is because, although the body can manufacture most of the molecules it needs, some essential molecules cannot be made in the body. These molecules are called essential nutrients, and must be provided by our diet.

The levels of essential nutrients that are required to maintain good health vary considerably depending on factors such as age and gender. Other relevant factors are size and metabolic rate. The control of adequate nutrient levels is further complicated by interactions between components of the diet that may alter the efficiency of absorption or utilisation of a particular nutrient. The body also has stores of certain nutrients so that some variation in the daily intake of such nutrients can be accommodated.

Although whole food sources are the best sources of nutrients, they are not typically eaten in sufficient amounts to provide sufficient amounts of nutrients. In addition, changes in eating patterns have created nutrient deficiencies and/or excesses which make it difficult to ensure all required nutrients are obtained. Consequently, it can be difficult to maintain a well balanced diet.

In addition to humans, various animal species including domestic pets, livestock and other farmed animals may suffer from nutrient deficiencies in their diets.

Deficiencies in essential nutrients can lead to poor health and even disease. For example, anaemia can be caused by a deficiency of iron or by a deficiency in vitamin $B_{12}$ and folic acid. An iron deficiency can cause defective proliferation and maturation of red cells, while deficiencies in vitamin $B_{12}$ and folic acid may result in a failure of red blood cells to mature, resulting in anaemia. Another example is scurvy, which is caused by a deficiency of vitamin C. Scurvy can cause tiredness, muscle weakness, joint and muscle aches, a rash on the legs and bleeding gums Supplementing a diet with particular vitamins and nutrients could prevent some conditions from developing or may provide significant health benefits. For example, calcium supplements may prevent osteoporosis, while folate may be taken by women before and during pregnancy to minimise the risk of neural tube disorders in infants. As another example, omega-3 fatty acid supplements can lower levels of heart disease and stroke as well as having anti inflammatory and brain/memory function benefits, while lycopene supplements may be able to reduce the risk of prostate cancer in Caucasian males. Increasing attention is being focussed on Vitamin D deficiency in humans, and correlations have been drawn between this deficiency and poor bone health (among others).

Selenium is an essential element for humans and animals. In the body selenium helps prevent damage by free radicals (i.e. acts as an antioxidant). It also has varied applications and uses in animal feed. For example, selenium may be utilised in specialised feeds for horses to aid in muscle problems (tying up) that may be due to a wide range of causes, which include exercise in excess of training level, respiratory infections, lack of dietary selenium/vitamin E, electrolytes & minerals.

Carotenoids such as lutein and zeaxanthin have antioxidant functions in maintaining eye health. In particular, carotenoids have been found to improve and protect the macular region by increasing the density of macular pigment, which absorbs harmful blue light and reduces oxidative damage. High dietary intake of carotenoids such as lutein and zeaxanthin may also protect against macular degeneration.

Beta-Carotene is a carotenoid which, in addition to the eye health properties indicated above, is also an antioxidant and boosts the immune system in humans and animals. It has been found that supplementing cattle with antioxidants such as beta-carotene, vitamin E, selenium may reduce somatic cell counts and improve the health of cattle with mastitis infections. It has also been found that when beta-carotene supplements are used, vitamin E supplements are also necessary, as the beta-carotene appears to reduce the level of vitamin E in the blood (body).

In addition supplementation is increasingly being addressed by the fortification of foods with vitamins and nutrients (such as in functional foods). As one example, direct supplementation of vitamins and nutrients to animals has been reported to increase nutritional concentrations in the foods produced from those animals, including meat, milk and eggs.

Many supplements containing nutraceutical actives providing vitamins, minerals and nutrients are currently available. However, there are problems associated with the bioavailability of some nutraceutical actives. As one example, nutraceutical actives may be poorly bioavailable due to their hydrophobicity (i.e. poorly water solubility). Nutraceutical actives that are not readily bioavailable need to be administered in large amounts in order to ensure that a sufficient amount of the vitamin and/or nutrient is absorbed. This can increase the cost of the dose of a nutraceutical active quite dramatically, particularly if the nutraceutical active is difficult to isolate or expensive to purchase. It may also mean that multiple and/or large capsules need to be administered. Accordingly, there is a need for improved or alternative active compositions having improved bioavailability.

In this specification where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

SUMMARY

It has surprisingly been found that a carrier comprising non-neutralised tocopheryl phosphate and a hydrophobic vehicle is suitable for delivery of nutraceutical and cosmeceutical actives.

Accordingly, a first aspect of the present relates to a carrier for the delivery of a nutraceutical or cosmeceutical active comprising non-neutralised tocopheryl phosphate and a hydrophobic vehicle.

The present invention provides a carrier for the delivery of a nutraceutical or cosmeceutical active comprising non-neutralised tocopheryl phosphate and a hydrophobic vehicle, wherein the non-neutralised tocopheryl phosphate comprises a mixture of mono-(tocopheryl)phosphate and di-(tocopheryl)phosphate.

The pH of the non-neutralised tocopheryl phosphate may be in the range of about 2 to about 4, or about 2 to about 3. Preferably, the pH of the non-neutralised tocopheryl phosphate is about 2 or about 3.

The non-neutralised tocopheryl phosphate may comprise compounds selected from the group consisting of mono-(tocopheryl)phosphate, mono-(tocopheryl)phosphate monosodium salt, mono-(tocopheryl)phosphate disodium salt, di-(tocopheryl)phosphate, di-(tocopheryl)phosphate monosodium salt, or a mixture thereof.

When the non-neutralised tocopheryl phosphate of the carrier composition comprises a mixture of a mono-(tocopheryl)phosphate to a di-(tocopheryl)phosphate, the ratio may be at least 2:1, within the range of about 4:1 to about 1:4, or within the range of about 6:4 to about 8:2. In preferred embodiments the ratio is about 6:4 or about 8:2.

The carrier may comprise non-neutralised tocopheryl phosphate from about 0.01% w/w up to about 40% w/w, from about 0.1% w/w up to about 5% w/w, from about 0.01% w/w up to about 5% w/w, from about 0.1% w/w up to about 2.5% w/w, from about 10% w/w up to about 30% w/w, or about 1% w/w, about 2% w/w, about 10% w/w or about 20% w/w of the total concentration of the carrier. In some embodiments the ratio (w/w) of non-neutralised tocopheryl phosphate to active may be from about 0.1:1 to about 100:1, from about 0.1:1 to about 5:1, from about 1:1 to about 5:1, from about 10:1 to about 60:1, or from about 30:1 to about 50:1. In some embodiments the ratio may be about 1:1, about 5:1, about 10:1, about 25:1 or about 40:1.

The hydrophobic vehicle may be an oil or a wax. The oil may be an edible oil such as a vegetable oil or a polyunsaturated oil containing polyunsaturated fatty acids, an essential or therapeutically-active oil, silicone oils, or an organic liquid (emollient). Preferably, the wax is beeswax.

The carrier may comprise a hydrophobic vehicle in an amount of at least about 80.0% w/w, at least about 90.5% w/w, at least about 99.0% w/w, or at least about 99.5% w/w, of the total concentration of the carrier. In some embodiments the hydrophobic vehicle is present in an amount of about 80.0% w/w, about 90.5% w/w, or about 99.5% w/w, of the total concentration of the carrier.

The carrier of the present invention is most suitable for enteral or parenteral administration of the nutraceutical or cosmeceutical active.

Accordingly, a second aspect of the present invention provides a formulation comprising the carrier and a nutraceutical or cosmeceutical active.

The formulation may be for topical, enteral or parental administration. Epicutaneus, oral and transdermal administration is preferred.

The nutraceutical and/or cosmeceutical active may be selected from the group consisting of vitamins, minerals, amino acids, herbs or other botanicals, metabolites, electrolytes, antioxidants, enzymes, organ tissues, gland extracts and prebiotics.

Preferably, the nutraceutical active is selected from the group consisting of $CoQ_{10}$ (ubiquinone), ubiquinol, omega-3 (DHA or EPA), lycopene, resveratrol, vitamin E, vitamin D, and carotenoids such as beta-carotene, lutein and zeaxanthin, and selenium such as sodium selenite.

The carrier may be prepared by a variety of techniques.

Accordingly, a third aspect of the present invention provides a method for preparing the carrier. In one embodiment, the method comprises the step of combining the components of the carrier, in suitable quantities, with stirring, until complete homogenisation is achieved. In a preferred embodiment, the method comprises the step of mixing the non-neutralised tocopheryl phosphate with the hydrophobic vehicle.

To prepare a formulation comprising the carrier and an active, the method comprises the further step of adding the active to the mixture, to the desired concentration, with gentle mixing.

For some applications it may be desirable for the formulation to comprise additional acceptable agents to form dry food compositions or drenches so as to make the formulation palatable or sufficiently acceptable or agreeable to the palate. Examples include dry food compositions comprised of solid material such as grains or rice and other nutritional requirements; or sugar syrups such as honey or molasses.

DETAILED DESCRIPTION

The present invention relates to a carrier for the delivery of nutraceutical and cosmeceutical actives which comprises non-neutralised tocopheryl phosphate and a hydrophobic vehicle wherein the non-neutralised tocopheryl phosphate comprises a mixture of mono-(tocopheryl)phosphate and di-(tocopheryl)phosphate. The carrier of the present invention is suitable for topical, enteral or parenteral administration of the nutraceutical and cosmeceutical actives to a subject. The term "subject" refers to any animal, in particular mammals such as humans, domestic pets, livestock and other farmed animals.

Non-Neutralised Tocopheryl Phosphate

The carrier of the present invention comprises non-neutralised tocopheryl phosphate.

Vitamin E exists in eight different forms, namely four tocopherols and four tocotrienols. Relevant to the present invention are the four tocopherols, which have a chroman ring with a hydroxyl group that can donate a hydrogen atom to reduce free radicals and a hydrophobic side chain which allows for penetration into biological membranes. Such derivatives of Vitamin E may be classified as "hydroxy chromans". The four tocopherols and four tocotrienols occur in alpha, beta, gamma and delta forms, determined by the number and location of methyl groups on the chroman ring. The tocopherol and tocotrienol forms of Vitamin E are shown by Formula (I):

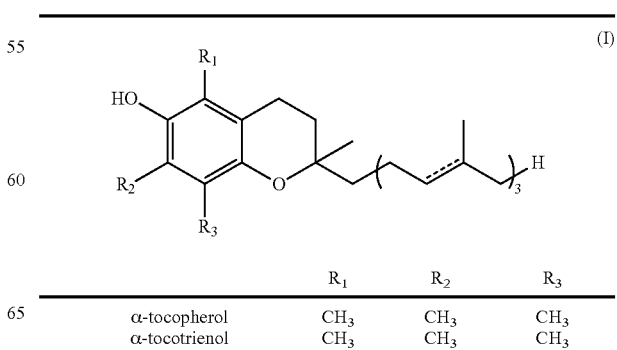

|  | $R_1$ | $R_2$ | $R_3$ |
|---|---|---|---|
| α-tocopherol | $CH_3$ | $CH_3$ | $CH_3$ |
| α-tocotrienol | $CH_3$ | $CH_3$ | $CH_3$ |

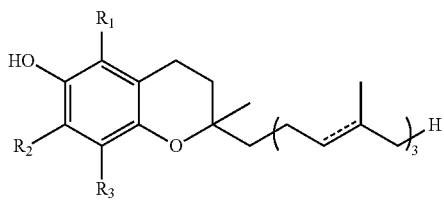

| | $R_1$ | $R_2$ | $R_3$ |
|---|---|---|---|
| β-tocopherol | $CH_3$ | H | $CH_3$ |
| β-tocotrienol | $CH_3$ | H | $CH_3$ |
| γ-tocopherol | H | $CH_3$ | $CH_3$ |
| γ-tocotrienol | H | $CH_3$ | $CH_3$ |
| δ-tocopherol | H | H | $CH_3$ |
| δ-tocotrienol | H | H | $CH_3$ |

Although the description herein refers to non-neutralised tocopheryl phosphate, this is by way of example only. It is to be appreciated that non-neutralised tocotrienyl phosphate may similarly be used in a carrier of the invention.

The term "tocopheryl phosphate" refers to any one of the tocopherols, as shown above, where a phosphate group ($PO_4$) is covalently bonded via the oxygen of the hydroxyl group of tocopherol or tocotrienol.

Tocopherol in the alpha, beta, gamma or delta form of tocopherol or a combination thereof may be phosphorylated by reaction with $P_4O_{10}$. The non-neutralised tocopheryl phosphate is the crude phosphorylation reaction product obtained prior to the neutralisation step.

The crude phosphorylation reaction product was previously regarded as being unstable and insufficiently pure for therapeutic use. However, it has now surprisingly been found that the crude phosphorylation reaction product can be used, and together with a hydrophobic vehicle may be used as a carrier for the delivery of nutraceutical or cosmeceutical actives and improve the bioavailability of the nutraceutical or cosmeceutical active formulated with the carrier. Surprisingly the inventor has also observed results that show that an oral dosage of non-neutralised tocopheryl phosphate per se or with hydrophobic vehicle (i.e. the carrier) causes particularly elevated levels of vitamin E in the blood.

As the non-neutralised tocopheryl phosphate is obtained before neutralisation, it has a pH of less than about 4 compared to "neutralized" tocopheryl phosphate which has a pH closer to neutral, usually in the range of above 5 to about 7. The pH of the non-neutralised tocopheryl phosphate is in the range of about 2 to about 4 or about 2 to about 3. Preferably, the pH of the non-neutralised tocopheryl phosphate is about 2 or 3.

Since tocopheryl phosphate can used without having to be neutralised and/or purified to separate the tocopheryl phosphate products, the preparation of this component of the carrier (i.e. the non-neutralised tocopheryl phosphate) involves fewer steps and is therefore much simpler and easier to produce thereby reducing general production costs. There is also minimal reduction in the overall product yield.

This crude phosphorylation reaction product may comprise a number of components including both mono- and di-phosphorylated tocopheryl phosphate. The non-neutralised tocopheryl phosphate may comprise compounds selected from the group consisting of mono-(tocopheryl) phosphate, mono-(tocopheryl)phosphate monosodium salt, mono-(tocopheryl)phosphate disodium salt, di-(tocopheryl) phosphate, di-(tocopheryl) phosphate monosodium salt, or a mixture thereof.

When the non-neutralised tocopheryl phosphate of the carrier composition contains a mixture of a mono-phosphate ester and a di-phosphate ester, for example a mono-(tocopheryl)phosphate and di-(tocopheryl)phosphate (which may be referred to as "TPM" herein), the ratio may be at least 2:1, within the range of about 4:1 to about 1:4, or within the range of about 6:4 to about 8:2. In one embodiment, the ratio may be about 6:4 or about 8:2.

The carrier may comprise non-neutralised tocopheryl phosphate from about 0.01% w/w up to about 40% w/w, from about 0.1% w/w up to about 5% w/w, from about 0.01% w/w up to about 5% w/w, from about 0.1% w/w up to about 2.5% w/w, from about 10% w/w up to about 30% w/w, or about 1% w/w, about 2% w/w, about 10% w/w or about 20% w/w, of the total concentration of the carrier.

In some embodiments the non-neutralized tocopheryl phosphate may be measured as a ratio to the active. This ratio is influenced by how the active formulates i.e. how much of the non-neutralised tocopheryl phosphate is required, and the delivery mode, for example a large volume may be required for the oral feed of a large animal. The ratio (w/w) of non-neutralised tocopheryl phosphate to active may be from about 0.1:1 to about 100:1, from about 0.1:1 to about 5:1, from about 1:1 to about 5:1, from about 10:1 to about 60:1, or from about 30:1 to about 50:1. In some embodiments the ratio may be about 1:1, about 5:1, about 10:1, about 25:1, or about 40:1.

Hydrophobic Vehicle

The carrier of the present invention also comprises a hydrophobic vehicle.

Some examples of hydrophobic vehicles which are most suitable include, but are not limited to, oils and waxes.

Suitable oil-based hydrophobic vehicles include any oil that is suitable for therapeutic use, such as for example, any edible oil. The oil-based hydrophobic vehicles may be natural or synthetic. The oil-based hydrophobic vehicles must also be compatible with non-neutralised tocopheryl phosphate, and the active formulated with the carrier.

Preferred oil-based hydrophobic vehicles suitable for use in the carrier of the present invention include vegetable, fruit, seed, grain or nut oils or the like. These oils may be saturated or unsaturated. These oils may also be winterised or non-winterised. Examples of suitable oils include canola oil, coconut oil, corn oil, cottonseed oil, olive oil, *Olea europaea* (Olive) leaf extract, palm oil, peanut oil, rapeseed oil, safflower oil, sesame oil, soybean oil, sunflower oil, almond oil, cashew oil, hazelnut oil, *macadamia* oil, *Macadamia integrifolia* (*Macadamia*) seed oil, mongongo nut oil, pecan oil, pine nut oil, pistachio oil, walnut oil, bottle gourd oil, buffalo gourd oil, pumpkin seed oil, watermelon seed oil, acai oil, blackcurrant seed oil, borage seed oil, evening primrose oil (*Oenothera biennis* oil), amaranth oil, apricot oil, apple seed oil, argan oil, artichoke oil, avocado oil (*Persea gratissima* oil), babassu oil, ben oil, borneo tallow nut oil, cape chestnut oil, cocoa butter, carob pod oil, cocklebur oil, cohune oil, coriander seed oil, dika oil, false flax oil, flax seed oil, grape seed oil (*Vitis vinifera*), hemp oil, kapok seed oil, lallemantia oil, marula oil, meadowfoam seed oil, mustard oil, nutmeg butter, okra seed oil, orange oil, papaya seed oil, *perilla* seed oil, pequi oil, pine nut oil, poppyseed oil, prune kernel oil, quinoa oil, ramtil oil, rice bran oil (for example, *Oryza* Satira™ Bran Oil), rose hip oil (*Rosa eglanteria* oil), royle oil, sacha inchi oil, sandalwood oil (*Santalum spicatum* oil), tea seed oil, thistle oil, tomato seed oil and wheat germ oil.

Suitable hydrophobic vehicles may also include cetearyl alcohol, cetearyl glucoside, cetearyl olivate, cocoyl proline, dicapryl ether, glycerin, glyceryl linoleate, glyceryl oleate, lactic acid, lecithin, pomegranite sterols, resveratrol and vitamin D3.

Suitable hydrophobic vehicles may also include polyunsaturated oils containing polyunsaturated fatty acids. In one or more embodiments, the unsaturated fatty acids are selected from the group of omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). In some instances, mixtures of fatty acids or medium chain triglycerides should not be used.

Another class of hydrophobic vehicles is essential oils, which may also be considered therapeutically-active oils if they contain active biologically occurring molecules and, exert a therapeutic effect on administration. In the context of the present invention, vehicles that additionally possess therapeutically beneficial properties may be referred to as "therapeutically-active vehicle". If a formulation is made using a therapeutically active vehicle, then the formulation will include non-neutralised tocopheryl phosphate, at least one nutraceutical or cosmeceutical active as well as the therapeutically active vehicle. Non-limiting examples of therapeutically active vehicles include essential oils such as rosehip oil, which contain retinoids and is known to reduce acne and post-acne scars, and tea tree oil, which possess antibacterial, antifungal and antiviral properties. Other examples of essential oils are oils of anise, basil, bergamot, camphor, cardamom, carrot, canola, *cassia*, catnip, cedarwood, citronella, clove, cypress, eucalyptus, frankincense, garlic, ginger, grapefruit, hyssop, jasmine, jojoba, lavender, lavandin, lemon, lime, mandarin, marjoram, myrrh, neroli, nutmeg, orange, peppermint, petitgrain, rosemary, sage, spearmint, star anise, tangerine, thyme vanilla, verbena and white clover.

Another class of therapeutically-active oils includes liquid hydrophobic plant derived oils, which are known to possess therapeutic benefits when applied topically.

Silicone oils also may be used and may be particularly desirable due to their known skin protective and occlusive properties. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)(diphenyl-siloxane) copolymers. Silicone oils may also considered therapeutically-active oil due to their barrier retaining and protective properties.

Hydrophobic liquids selected from the family of organic liquids described as "emollients" is another class of hydrophobic vehicles. Emollients possess a softening or soothing effect, especially when applied to body areas, such as the skin and mucosal surfaces. Examples of suitable emollients include isopropyl myristate, isopropyl palmitate, isopropyl isostearate, diisopropyl adipate, diisopropyl dimerate, maleated soybean oil, octyl palmitate, cetyl lactate, cetyl ricinoleate, tocopheryl acetate, cetyl acetate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, octyl dodecanol, sucrose esters of fatty acids and octyl hydroxystearate.

Suitable hydrophobic vehicles also include pharmaceutically acceptable waxes. An example of a suitable wax is beeswax.

The carrier may comprise a hydrophobic vehicle in an amount of at least about 60.0% w/w, at least about 80.0% w/w, at least about 90.5% w/w, at least about 99.0% w/w, or at least about 99.5% w/w, of the total concentration of the carrier. In some embodiments the hydrophobic vehicle is present in an amount of about 80.0% w/w, about 90.5% w/w, or about 99.5% w/w, of the total concentration of the carrier.

Administration Route

Routes of administration can broadly be divided into a three categories by effect, namely, "topical" where the desired effect is local, so the substance is applied directly where its action is desired, "enteral" where the desired effect is systemic (non-local) so the substance is given via the digestive tract, and "parenteral" where the desired effect is systemic, so the substance is given by routes other than the digestive tract.

The carrier of the present invention is suitable for topical, enteral or parenteral administration of the nutraceutical and cosmeceutical actives. Examples of topical routes of administration having a local effect include epicutaneous (onto the skin) and intravitreal (onto the eye).

Examples of enteral routes of administration having a systemic (non-local) effect include any form of administration that involves any part of the gastrointestinal tract, such as oral (into the mouth), intranasal (into the nose), rectal (into the rectum), and vaginal (into the vagina). Oral administration includes buccal administration (absorbed through the cheek near the gumline) and sublingual administration (under the tongue).

Examples of parenteral routes of administration by injection, infusion or diffusion having a systemic effect include intravenous (into a vein), intraarterial (into an artery), intramuscular (into a muscle), intracardiac (into the heart), subcutaneous (under the skin), percutaneous (via needlepuncture into the skin), intradermal (into the skin itself), intrathecal (into the spinal canal), intraperitoneal (infusion or injection into the peritoneum), intravesical infusion (infusion into the urinary bladder), epidural (injection or infusion into the epidural space), transdermal or transcutaneous (diffusion through the intact skin), transmucosal (diffusion through a mucous membrane), insufflation (diffusion through the nose), inhalational (diffusion through the mouth), sublingual (under the tongue), and buccal (absorbed through cheek near gumline).

Epicutaneus, oral and transdermal administration is preferred.

Nutraceutical or Cosmeceutical Actives

Nutraceutical or cosmeceutical actives may be formulated with a carrier of the present invention.

Nutraceutical actives are typically products that are enriched in nutrients to permit the nutraceutical active to be provided at a concentration that is much higher than that which can be provided by diet alone. The nutraceutical and/or cosmeceutical active may be selected from the group consisting of vitamins, minerals, amino acids, herbs or other botanicals, metabolites, electrolytes, anti oxidants, enzymes, organ tissues, gland extracts and prebiotics.

Suitable nutraceutical actives are those that would be suitable for formulation with non-neutralised tocopheryl phosphate and a hydrophobic vehicle. Poorly bioavailable nutraceutical actives that are poorly water-soluble and/or hydrophobic or water soluble and/or hydrophilic will be suitable for formulation with a carrier of the present invention.

Suitable nutraceutical actives include, but are not limited to fatty acids, fruit and vegetable extracts, vitamins, phospholipids, certain proteoglycans, certain amino acids, carotenoids, various food additives, various phytonutrients including phytosterols, certain antioxidants, plant oils, fish and marine animal oils, algae oils and essential elements.

The nutraceutical active may be a fat-soluble vitamin. Suitable fat-soluble vitamins include vitamin D (D2, D3 and their derivatives), vitamin E ($\alpha$, $\beta$, $\gamma$, $\delta$-tocopherols, or $\alpha$, $\beta$, $\gamma$, $\delta$-tocotrienols), vitamin A (retinol, retinal, retinoic acid), vitamin K ($K_1$, $K_2$, $K_3$ and their derivatives). It is to be noted that if the nutraceutical active is vitamin E, the unphosphorylated form of vitamin E is used.

The nutraceutical active may also be a phospholipid. The phospholipid may be phosphatidyl and the proteoglycans may be chondroitin.

The nutraceutical active could also be coenzyme $Q_{10}$ (or ubiquinone), ubiquinol or resveratrol; a carotenoid, which may be selected from $\alpha$, $\beta$, or $\gamma$-carotene, lycopene, lutein, zeaxanthin and astaxanthin; a phytonutrient, which may be selected from lycopene, lutein and seaxanthin; an unsaturated fatty acid, which may be linoleic acid, conjugated linoleic acid, linolenic acid, omega-3 fatty acids including but not limited to docosahexaenoic acid (DHA) and eicosapentaeonic acid (EPA) and their glycerol-esters.

The nutraceutical active may also be a phytoestrogen, such as a phytosterol. Suitable phytosterols may be selected from 3-sitosterol, campesterol and stigmasterol, isoflavones, stilbenes, lignans and coumestans and others. Suitable isoflavones may be selected from genistein and daidseln. A suitable stilbene may be trans-resveratrol. A suitable lignan may be mataresinol. A suitable coumestan may be selected from coumostrol.

The nutraceutical active may also be a bioactive peptide, such as casein-phosphopeptide (CPP) and other calcium-binding peptides.

The nutraceutical active may also be a micronutrient, such as a trace element or an essential element. The trace element may be iron cobalt, chromium, copper, iodine, manganese, selenium, zinc or molybdenum or a salt thereof. For example, if the trace element is selenium, the selenium may be provided in the form of a salt, such as sodium selenite.

In one embodiment, the nutraceutical active is selected from the group consisting of $CoQ_{10}$ (ubiquinone), ubiquinol, omega-3 (DHA or EPA), lycopene, resveratrol, vitamin E, vitamin D, and caratenoids such as beta-carotene, lutein, zeaxanthin and sodium selenite.

Cosmeceutical actives are cosmetic products with biologically active ingredients purporting to have medical or drug-like benefits. Cosmeceutical actives generally improve the skin's appearance by providing ingredients necessary for healthy skin.

Suitable cosmeceutical actives are those that would be suitable for formulation with non-neutralised tocopheryl phosphate and a hydrophobic vehicle. In some circumstances hydrophilic actives may be able to be used. However, it is likely that cosmeceutical actives that are poorly water-soluble and/or hydrophobic, and thus have poor bioavailability, will be most suitable for formulation with a carrier of the present invention.

Many of the nutraceutical actives described above may also be useful as cosmeceutical actives to provide therapeutically beneficial effects to the body, internally for well-being and externally such as on the skin. Accordingly, suitable cosmeceutical actives may be selected from the group of nutraceutical actives defined above.

In addition to the nutraceutical actives defined above, the cosmeceutical active may preferably be selected from the group consisting of Aloe vera, Ascorbyl palmitate (Vitamin C), Beta carotene (Vitamin A), Beta glucan, Bisabolol, *Camellia thea* (green tea) extract, Capric/Caprylic triglycerides, *Centella asiatica* (Gotu cola) Extract, Cetearyl olivate, Chlorophyll, *Citrus sinensis* (orange) oil, Cocoyl proline, Dicapryl ether, Disodium lauriminodipropionate tocopheryl phosphates (Vitamin E phosphates), Glycerin, Glyceryl linoleate (Omega 6 fatty acids Vitamin F), Glyceryl oleate, *Glycyrrhiza glabra* (Licorice) Root Extract, *Hamamelis virgiana* (Witch hazel) extract, Lactic acid, Lecithin, Lutein, *Macadamia integrifolia* (*Macadamia*) seed oil, *Matricaria chamomilla* (Chamomile) extract, *Oenothera biennis* (Evening primrose) Oil, *Olea europaea* (Olive) leaf extract, Rice bran oil, *Tocotrienols, Persea gratissima* (Avocado) Oil, *Polygonum multiflorum* extract, *Pomegranate sterols, Resveratrol, Rosa eglanteria* (Rose hip) oil, *Santalum spicatum* (Sandalwood) oil, Titanium dioxide, Tocopherol (alpha, delta, gamma, beta natural vitamin E), Tocopheryl phosphates (alpha), Vitamin A palmitate, Vitamin D3, *Vitis vinifera* (Grapeseed) oil and Zinc oxide.

It is also to be understood that derivatised forms of the nutraceutical or cosmeceutical actives described above are included within the scope of the present invention. For example, "nutraceutically or cosmeceutically acceptable derivatives", "nutraceutically or cosmeceutically acceptable salts", "nutraceutically or cosmeceutically acceptable esters" and "nutraceutically or cosmeceutically acceptable prodrugs" of the actives as described below.

The term "nutraceutically or cosmeceutically acceptable derivatives" includes, but is not limited to, nutraceutically or cosmeceutically acceptable salts, esters, salts of such esters, ethers, or any other derivative including prodrugs and metabolites, which upon administration to a subject in need is capable of providing, directly or indirectly, a biologically active compound as otherwise described herein.

As used herein, the term "nutraceutically or cosmeceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Nutraceutically or cosmeceutically acceptable salts are well known in the art. For example, S. M. Berge, et al. describe acceptable salts in detail in J. Pharmaceutical Sciences, 66:1-19, 1977. Examples of nutraceutically or cosmeceutically acceptable nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other nutraceutically or cosmeceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Representative alkali or alkaline earth metal salts include sodium, lithium, potassium, calcium, magnesium, and the like. Further nutraceutically or cosmeceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "nutraceutically or cosmeceutically acceptable ester" refers to esters which are hydrolysed in vivo and include those that break down readily in the human body to leave the parent compound or a salt thereof. Suitable ester groups include, for example, those derived from nutraceutically or cosmeceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "nutraceutically or cosmeceutically acceptable prodrugs" as used herein refers to those prodrugs of the biologically active compounds which are, within the scope of sound medical judgment, suitable for use in contact with the tissues of a subject with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

It is also possible that a combination of any of the nutraceutical actives and/or cosmeceutical actives described above may be formulated with a carrier of the present invention to permit the simultaneous delivery of multiple nutraceutical actives in a single formulation. It therefore should be noted that, as used in the present specification, the singular forms "a", "an" and "the" include plural aspects unless the context clearly dictates otherwise. Thus, for example, reference to "a nutraceutical active" or a "cosmeceutical active" includes a single nutraceutical active, a single cosmeceutical active, two or more nutraceutical actives; two or more cosmeceutical actives; one or more nutraceutical actives and one or more cosmeceutical actives; and so forth for other features of the invention.

The amount of nutraceutical or cosmeceutical active should be sufficient to provide a therapeutic effect or an amount suitable to permit a subject (e.g. human or animal) to obtain their recommended daily dosage of the nutraceutical active in an appropriate amount of dosages per day. The actual amount of the nutraceutical active will also depend on the particular nutraceutical active being used.

The amount of nutraceutical or cosmeceutical active used in the formulation may also be expressed as a ratio of the amount of non-neutralised tocopheryl phosphate to the amount of the nutraceutical or cosmeceutical active. In some applications the non-neutralized tocopheryl phosphate may be measured as a ratio to the active. This ratio is influenced by how the active formulates i.e. how much of the non-neutralised tocopheryl phosphate is required, and the delivery mode, for example a large volume may be required for the oral feed of a large animal. The ratio (w/w) of non-neutralised tocopheryl phosphate to active may be from about 0.1:1 to about 100:1, from about 0.1:1 to about 5:1, from about 1:1 to about 5:1, from about 10:1 to about 60:1 or from about 30:1 to about 50:1. In some embodiments the ratio may be about 1:1, about 5:1, about 10:1, about 25:1 or about 40:1.

In one example, where the nutraceutical active is vitamin D3, the ratio of non-neutralised tocopheryl phosphate to vitamin D3 may be within the range of about 1:1 to about 60:1, about 1:1 to about 40:1, or less than 40:1, or between about 1:1 and about 20:1, between about 1:1 and about 10:1, or between about 1:1 and about 5:1.

The following description of preferred embodiments of the invention refers to two specific nutraceutical actives by way of example in order to further describe the invention.
Coenzyme $Q_{10}$ (or $CoQ_{10}$)

$CoQ_{10}$ also known as ubiquinone is a naturally occurring coenzyme found in aerobic organisms. The primary role is a vital intermediate of the electron transport system in the mitochondria, acting as an anti-oxidant by scavenging free radicals, and as a stabiliser of cell membrane structure. Adequate amounts of $CoQ_{10}$ are necessary for cellular respiration and ATP production, and therefore $CoQ_{10}$ functions as an intercellular antioxidant.

$CoQ_{10}$ plays an essential role in the production of energy in heart cells, and helps to maintain a healthy cardiovascular system. Clinical studies have shown that there is a correlation between cardiovascular disease and low tissue levels of $CoQ_{10}$. Natural levels of $CoQ_{10}$ decline as we age, and can also decline if we are taking certain medications, such as statins to lower the cholesterol levels in people with or at risk of cardiovascular disease. There is therefore a benefit associated with restoring the levels of $CoQ_{10}$ in the body.

$CoQ_{10}$ is an extremely water insoluble nutraceutical active, and is therefore poorly absorbed from dietary sources (i.e. only about 5 to 10% of the $CoQ_{10}$ is bioavailable). The $CoQ_{10}$ used to prepare nutraceutical products is typically very expensive as $CoQ_{10}$ is readily degraded due to its light and oxygen sensitivity. Production of $CoQ_{10}$ is therefore quite laborious and requires nitrogen blanketing procedures to ensure that the stability and/or activity of $CoQ_{10}$ is maintained. Although there are numerous $CoQ_{10}$ products available on the market, the oral bioavailability of these products is low due to the low water solubility of $CoQ_{10}$ used in these formulations. It is therefore necessary to use excesses of $CoQ_{10}$ in order to ensure that sufficient amounts of $CoQ_{10}$ are delivered. Alternative approaches to the delivery of $CoQ_{10}$ use nanotechnology to improve the bioavailability of $CoQ_{10}$, however, such approaches also add to the cost.

Omega-3

Omega-3 polyunsaturated fatty acids are essential fatty acids which must be obtained via dietary sources since they cannot be manufactured by the body. Omega-3 fatty acids are most often found in fish oil, but may also be manufactured commercially. Long chain omega-3 fatty acids include DHA and EPA. DHA is widely believed to provide healthy brain development, particularly in young children, can support fetal and maternal development and enhance skin and eye function.

Scientific research indicates benefits from omega-3 supplementation in human conditions including cardiovascular disease, rheumatoid arthritis, and high blood pressure. Deficiency of omega-3 may contribute to the development of psychiatric disorders including depression, bipolar disorder, schizophrenia, dementia, dyslexia and postpartum psychiatric disorders.

Omega-3 has extremely low water solubility and thus the oral bioavailability of omega-3 is quite low. Approximately 1-3 g of Omega-3 is recommended in order to allow adequate intake given the low bioavailability and problems associated with formulation of Omega-3. Accordingly, administration of Omega-3 must either be via very large single dose capsules or via multiple capsules (3-6 capsules, depending on the brand and/or formulation). Another problem associated with the administration of omega-3 is the fish aftertaste, which can be very undesirable for people to take. There is therefore a need for an improved formulation for the delivery of $CoQ_{10}$.

Selenium

Selenium is an essential element for humans and animals. In the body selenium helps prevent damage by free radicals (i.e. acts as an antioxidant). It also has varied applications and uses in animal stockfeed, i.e. For example, selenium may be utilised in specialised feeds for horses to aid in muscle problems (tying up) that may be due to a wide range of causes, which include i.e. exercise in excess of training level, respiratory infections, lack of dietary selenium/vitamin E, electrolytes & minerals.

Carotenoids

Carotenoids such as lutein and zeaxanthin have antioxidant functions in maintaining eye health. In particular, carotenoids have been found to improve and protect the macular region by increasing the density of macular pigment, which absorbs harmful blue light and reduces oxidative damage. High dietary intake of carotenoids such as lutein and zeaxanthin may also protect against macular degeneration.

Beta-carotene is a carotenoid which, in addition to the eye health properties indicated above, it is also an antioxidant and boosts the immune system in humans and animals. It has been found that supplementing cattle with antioxidants such as beta-carotene, vitamin E, selenium may reduce somatic cell counts and improve the health of cattle with mastitis infections. It has also been found that indicate when beta-carotene supplements are used, vitamin E supplements are also necessary, as the beta-carotene appears to reduce the level of vitamin E in the blood (body).

Dosage Form

Compositions comprising the carrier may be prepared into any suitable dosage form for enteral or parenteral administration and/or for delivery of nutraceutical or cosmeceutical actives.

A person skilled in the art would readily appreciate what would be a suitable dosage form for enteral or parental administration.

Suitable dosage forms for enteral administration would include but not be limited to capsules, tablets, pills, or specialty tablets such as buccal, sublingual, chewable tablets or orally-disintegrating tablets. Another example of a suitable dosage form would be edible thin films.

Other suitable dosage forms for enteral administration include liquid solutions or suspensions. Suitable liquid solution or suspension dosage forms may be in the form of a drink, such as sports drinks containing electrolytes (e.g. gatorade), or syrup and elixirs. Other suitable liquid solution or suspension dosage forms include nasal delivery solutions and oral suspensions. Specifically liquid solutions or suspensions in the form of a "drench" may be suitable for use with large animals such as cows.

The dosage form for enteral administration may also be a powder or solid crystal, which can be either dissolved or suspended in a liquid before administration. Alternatively, the powder may be consumed directly or added to a food or drink product for consumption. In the case of farm animals, the formulation may be added directly to the dry feed or in pelleted form.

Particularly in the case of a domestic or farm animal, the dosage form may include injection.

In another example, the dosage form for enteral administration may be a food to which the composition is added before the food is consumed. For example, the food product may for example be a bar such as a health bar, a cereal, bread such as a fortified bread, a cookie, a spread such as butter, a dairy product such cheese or milk, or any other suitable food product.

Where the composition has a disagreeable taste, additives with sufficient flavour to disguise the bad taste may be added to the dosage form (e.g. masking agents).

Examples of suitable dosage forms for parenteral administration include but are not limited to injectables (i.e. solutions, suspensions, emulsions, and dry powders for reconstitution), intramammary infusions, intravaginal delivery systems, and implants.

Preparation of the Carrier

A carrier of the present invention may be prepared by a variety of techniques.

One method of preparing the carrier involves combining the components of the carrier, in suitable quantities, with stirring, until complete homogenisation is achieved. In this method, it may also be desirable that the non-neutralised tocopheryl phosphate is added to the hydrophobic vehicle and warmed to a temperature of 80° C. or less. Heating however may not always be necessary or desirable. To prepare a formulation comprising the carrier and an active, the active may be added to the mixture described above when it is being warmed, to the desired concentration, with gentle mixing. Alternately the mixture may be cooled prior to addition of the active, particularly when the active is heat labile.

A carrier, or a formulation which comprises the carrier and an active, can optionally further comprise one or more excipients. A person skilled in the art of the invention would appreciate suitable excipients which could be included in the carrier of the invention. The choice and amount of excipients will depend on the intended use of the carrier, mode of administration and/or dosage form.

Examples of suitable excipients include additional solvents such as water, thickeners or gelling agents, surfactants, buffers, emollients, sweeteners, disintegrators, flavours, colours, fragrances, electrolytes, appearance modifiers, film foaming polymers and the like. Suitable sweeteners include sucrose, lactose, glucose, aspartame or saccharin. Suitable disintegrators include corn starch, methylcellulose, polyvinylpyrrolidone, xanthan gum, bentonite, alginic acid or agar. Suitable flavours include peppermint oil, oil of wintergreen, cherry, orange or raspberry flavouring. Suitable preservatives include sodium benzoate, methylparaben, propylparaben, and sodium bisulphite. However, it will be appreciated that any excipients which have been approved for use in nutraceutical and cosmeceutical products by the regulatory bodies may be employed in the compositions of the present invention.

Advantages

The carrier of the present invention comprises non-neutralised tocopheryl phosphate and a hydrophobic vehicle, and is particularly suitable for formulation with a nutraceutical or cosmeceutical active.

It has been found that the combination of non-neutralised tocopheryl phosphate and a hydrophobic vehicle is able to increase the bioavailability of the active especially over a 24 hour period, compared to other known active formulations, which is highly desirable. Accordingly, when formulations of the present invention are provided to a subject, more of the active is bioavailable and therefore, the active can be delivered more effectively. The consequence of this is that a greater proportion of the active is present in a single dose, and thus the amount of active needed for effective daily dosing can be reduced. Furthermore, since the improvement provided by the formulation of the present invention may be considered to be an improvement in acute delivery of an active to a subject, for a nutraceutical active, a single delivery of the formulation provides a more rapid intake of the nutraceutical active and thus allows rapid replenishment of the subject's stores of the nutraceutical active. For cosmeceutical actives, an increased therapeutically beneficial effect can be obtained with a lesser amount of the formulation.

FIGURES

The invention is described further by way of example with reference to the accompanying drawings in which.

EXAMPLES

Figure 1:
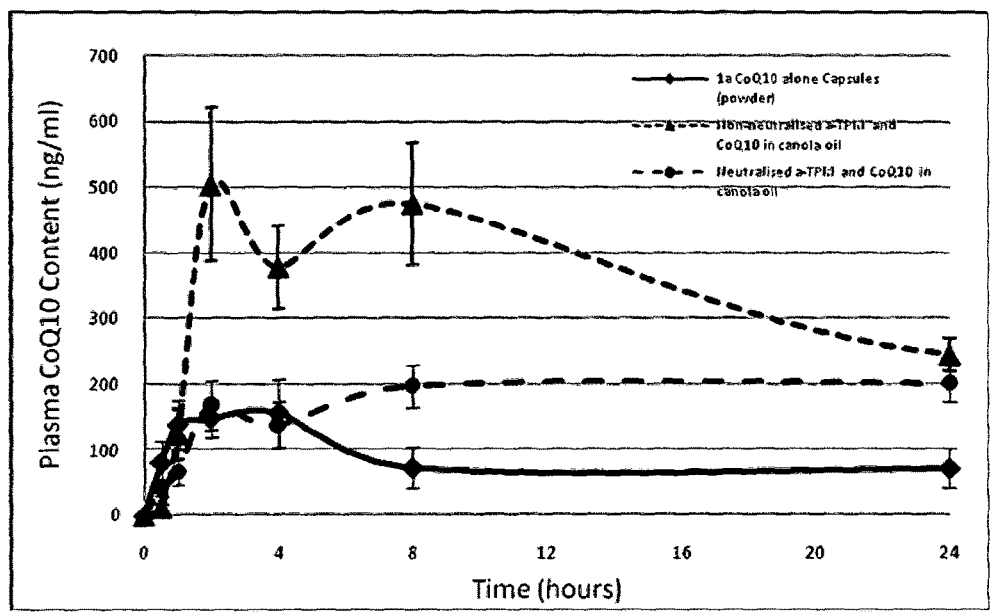
FIG. 1 is a graph showing the plasma $CoQ_{10}$ concentration (ng/ml) measured in rats treated with nutraceutical compositions over a 24 hour period.

The invention is described further by reference to the following non-limiting examples of the invention.

Example 1: $CoQ_{10}$

In the present example the inventor(s) investigated the oral delivery of compositions comprising the nutraceutical $CoQ_{10}$ where supplementation was a single dose measured over 24 hours. The present example is an in vivo study in which rats are used to examine the bioavailability of various $CoQ_{10}$ compositions.
Materials
The α-tocopherol used in the present study was obtained from ADM, Australia. The non-neutralised α-tocopheryl phosphate was prepared from the α-tocopherol starting material by Phosphagenics. The neutralised α-tocopheryl phosphate was prepared by Phosphagenics for use in the preparation of formulation 1c.

The $CoQ_{10}$ used in the present study was obtained from Pure Bulk CAS#303-98-0. The $CoQ_{10}$ powder was bright orange in colour.

The canola oil used in the present study was obtained from Cargill Health and Nutrition.
Methods
The following 4 formulations were tested in the present example:
1a: $CoQ_{10}$ alone capsules (powder);
1b: Non-neutralised α-TP and $CoQ_{10}$ as a liquid in canola oil;
1c: Neutralised α-TPH and $CoQ_{10}$ as a liquid in canola oil; and The formulations 1a to 1c have been designed to deliver 5 mg $CoQ_{10}$ in each dose.

| Formulation | 1a | 1b | 1c |
|---|---|---|---|
| Amount of $CoQ_{10}$ | 5 mg | 0.5 ml of a 10/mg/ml stock formulation | 0.5 ml of a 10/mg/ml stock formulation |
| Amount of non-neutralised α-TP | — | 0.5 ml of a 10/mg/ml stock formulation | — |
| Amount of neutralised α-TP | — | — | 0.5 ml of a 10/mg/ml stock formulation |
| Amount of Canola Oil | — | 0.5 ml delivered per rat | 0.5 ml delivered per rat |

The 3 formulations were prepared as described below.

Formulation 1a: is a powder preparation which was provided to the animals in capsule form. The capsules were prepared by packing empty capsule shells with 5 mg of powdered $CoQ_{10}$.

Formulation 1b: is a liquid preparation which was provided to the animals in liquid form. A 10 mg/ml solution of non-neutralised α-tocopheryl phosphate in Canola oil was prepared, to which was added 10 mg of $CoQ_{10}$ per ml of the non-neutralised α-tocopheryl phosphate in Canola mixture at 40° C. with gentle stirring until the powders were dissolved.

Formulation 1c: is a liquid preparation which was provided to the animals in liquid form. The formulation was first prepared by a 10 mg/ml solution of neutralised α-tocopheryl phosphate in Canola oil was prepared, to which was added 10 mg of $CoQ_{10}$ per ml of the neutralised α-tocopheryl phosphate in Canola mixture at 40° C. with gentle stirring until the powders were dissolved.

Male Sprague-Dawley Rats weighing no more than 400 g were obtained, housed (2-3 rats per box) and were fed ad libitum. The rats were acclimatised for a minimum of 7 days and then randomised into groups for treatment with each of the 3 formulations described above. Formulations 1a and 1c were each administered to treatment groups having nine rats each. Formulation 1b was administered to a treatment group having ten rats.

Once acclimatised, the rats were pre-bled with tail bleeding to establish $CoQ_{10}$ levels at time zero values before a treatment dose was delivered. After the initial blood collection each rat in their respective treatment group was given a dose of treatment orally either in capsule form or liquid form. Following treatment blood samples were collected at various time points: 0.5 hr, 1 hr, 2 hr, 4 hr, 8 hr, and 24 hr (1 day). Over the period of blood collection the rats were administered a single dose of treatment.

Blood samples were collected in lithium heparin blood collection Capiject™ tubes. Once blood was collected the blood samples were placed on ice and centrifuged at 4° C. for 5 minutes at 8,000 rpm. The plasma was then removed from the tubes and placed in new eppendorf tubes for storage at −20° C. Plasma samples were then analysed by HPLC to determine the amount of $CoQ_{10}$ released in the plasma.
Results
Basal $CoQ_{10}$ levels in the Sprague-Dawley rats used were seen to be on average between 100-150 ng/ml. The results shown for supplementation are subtracted values and therefore indicate the basal values for each treatment as zero ng/ml.

The effect of formulations 1a to 1c on the bioavailability of $CoQ_{10}$ in the blood of Sprague-Dawley rats was examined over the 24 hour treatment period.

Bioavailability Comparison Over a 24 Hour Treatment Period

The graph shown in FIG. 1 shows the improvement in bioavailability obtained when the $CoQ_{10}$ formulation includes non-neutralised α-tocopheryl phosphate and an oil carrier (i.e. formulation 1b), when compared to formulations containing $CoQ_{10}$ alone (formulation 1a) and $CoQ_{10}$ and neutralised/purified α-tocopheryl phosphate in canola oil (formulation 1c).

Over the 24 hours of treatment, formulation 1b provided the best improvement in bioavailability of $CoQ_{10}$.

Conclusion

Supplementation using formulation 1a (the powdered form of $CoQ_{10}$ alone in capsules) provided a peak plasma level of $CoQ_{10}$ approximately 4 hrs-post dosing.

Formulation 1b (non-neutralised α-TP and $CoQ_{10}$ in canola oil) had significantly higher overall concentration of $CoQ_{10}$ in the plasma compared to formulation 1a ($CoQ_{10}$ alone in capsules) during the entire 24 hour period post-dosing. Formulation 1c (neutralised α-TP and $CoQ_{10}$ in canola oil) performed less well than formulation 1b (non-neutralised α-TP and $CoQ_{10}$ in canola oil).

The canola oil used in the present study was obtained from Cargill Health and Nutrition.

Methods

The following 6 formulations were tested in the present example:

2a: Low dose omega-3 (DHA) alone as a liquid in canola oil;
2b: Low dose omega-3 (DHA) and low dose non-neutralised α-tocopheryl phosphate as a liquid in canola oil;
2c: Low dose omega-3 (DHA) and high dose non-neutralised α-tocopheryl phosphate as a liquid in canola oil;
2d: Low dose omega-3 (DHA) and high dose TPM neutralised α-tocopheryl phosphate as a liquid in canola oil;
2e: High dose omega-3 (DHA) alone as a liquid in canola oil; and
2f: High dose omega-3 (DHA)+low dose TPM non-neutralised α-tocopheryl phosphate as a liquid in canola oil.

Formulations 2a to 2d delivered the low omega-3 (DHA) dose, which was 88.6 mg/kg (HED=1 g/day). Formulation 2a included omega-3 alone, while formulations 2b to 2c included non-neutralised α-tocopheryl phosphate having an omega-3: non-neutralised α-tocopheryl phosphate ratio varying from 1:0.1 to 1:0.5. Formulation 2d included neutralised α-tocopheryl phosphate.

Formulation 2e included omega-3 alone, while formulation 2f included non-neutralised α-tocopheryl phosphate. Formulations 2e and 2f delivered the high omega-3 (DHA) dose, which was 265.7 mg/kg (HED=3 g/day). The ratio of omega-3:TPM in formulation 2d was 1:0.1.

|  | Formulation | | | | | |
| --- | --- | --- | --- | --- | --- | --- |
|  | 2a | 2b | 2c | 2d | 2e | 2f |
| Amount of omega-3 | 44.3 mg/ml | 44.3 mg/ml | 44.3 mg/ml | 44.3 mg/ml | 132.9 mg/ml | 132.9 mg/ml |
| Amount of non-neutralised α-TP | — | 4.4 mg/ml | 22.2 mg/ml | — | — | 13.3 mg/ml |
| Amount of neutralised α-TP | — | — | — | 22.2 mg/ml | — | — |
| Amount of Canola Oil | 0.5 ml delivered per rat | 0.5 ml delivered per rat | 0.5 ml delivered per rat | 0.5 ml delivered per rat | 0.5 ml delivered per rat | 0.5 ml delivered per rat |

Formulation 1b, provides a significant increase in the peak plasma $CoQ_{10}$ concentrations, over a 24 hour period following a single dose of the formulation.

Example 2: Omega-3

In the present example we investigated the oral delivery of new formulations of the nutraceutical omega-3 over following a single does of supplementation over a 24 hour period. The present study is an in vivo study in which rats are used to examine the bioavailability of various omega 3 formulations compared with the non-neutralised alpha-tocopheryl phosphate.

Materials

The α-tocopherol used in the present study was obtained from ADM, Australia. The non-neutralised α-tocopheryl phosphate was prepared from the α-tocopheryl starting material by Phosphagenics. The neutralised α-tocopheryl phosphate was prepared by Phosphagenics for use in the preparation of formulation 2d.

The omega-3 used in the present study was obtained from Croda, and contains a minimum omega-3 content of 600 mg/g, a minimum EPA content of 60 mg/g and a minimum DHA content of 500 mg/g.

These 6 formulations were prepared as described below.

In each case for the formulations below, this is how the formulations were made.

Omega-3 stocks were made in canola oil, i. Low (44.3 mg/ml) & ii. High 132.9 mg/ml these were simply added will gentle mixing at 40° C. and then these were subdivided into smaller aliquots (~20 ml each).

The low omega-3 dose was divided into 4×20 ml lots for formulations:

2a: Low omega alone (20 ml)—no further additions
2b: Low omega-3 (20 ml) plus 88 mg (4.4 mg/ml) of the non-neutralised alpha-TPM,
2c: Low omega-3 (20 ml) plus 444 mg (22.22 mg/ml) of the non-neutralised alpha-TPM,
2d: Low omega-3 (20 ml) plus 444 mg (22.2 mg/ml) of the neutralised alpha-TPM The high omega-3 dose was divided into 2×20 ml lots for formulations:

2e: High omega alone (20 ml)—no further additions
2f: High omega-3 (20 ml) plus 266 mg (13.3 mg/ml) of the non-neutralised alpha-TPM.

Formulation 2a and 2e: is a liquid preparation which was provided to the animals as a liquid. The formulation was prepared by adding omega-3 to Canola oil to a concentration of 44.3 mg/ml for formulation 2a and 132.9 mg/ml for formulation 2e and each of these formulations were mixed gently at 40° C.

Formulation 2b, 2c and 2f: is a liquid preparation which was provided to the animals in liquid form. The formulation was prepared by adding omega-3 to Canola oil to a concentration of 44.3 mg/ml for formulations 2b and 2c and a concentration of 132.9 mg/ml for formulation 2f. To each of these formulations was added non-neutralised α-tocopherol phosphate. The non-neutralised α-tocopherol phosphate was added to formulation 2b to a concentration of 4.4 mg/ml, to formulation 2c to a concentration of 22.2 mg/ml and to formulation 2f to a concentration of 13.3 mg/ml. Each of these formulations was gently mixed at 40° C.

Formulation 2d: is a liquid preparation which was provided to the animals in liquid form. The formulation was prepared by adding omega-3 to Canola oil to a concentration of 44.3 mg/ml. Neutralised α-tocopherol phosphate was added to this formulation to a concentration of 22.2 mg/ml. The formulation was gently mixed at 40° C.

Male Sprague-Dawley rats weighing between 200-300 g were obtained from the ARC, Perth Australia and were housed 2-3 rats per cage and were fed ad libitum. The rats were acclimatised for a minimum of 7 days before the experiments were conducted. The rats were then randomised and set-up into the following treatment groups (7-10 rats/group). Formulations 2a, 2c and 2e were each administered to treatment groups having nine rats each. Formulation 2b, 2d and 2f were each administered to treatment groups having seven, ten and eight rats, respectively.

Following acclimatisation and pre-bleeding, animals were dosed once and blood samples were collected into lithium heparin tubes at: 0.5, 1, 2, 4, 8 and 24 hours post dosing. Immediately after collection, blood samples were placed on ice and centrifuged at 4° C. for 5 min at 8,000 rpm. The plasma was collected and stored at −80° C. until the analysis on omega-3 content (DHA) were analysed.

The effect of the various omega-3 (DHA) formulations on the bioavailability of omega-3 (DHA) in the blood of SD rats was examined following a single dose of the formulation. The assessment took place over: 0, 0.5, 1, 2, 4, 8 and 24 hour time points analysing the amount of DHA present in the plasma of these animals following a single dose of the various formulations.

Results

Basal plasma concentration of DHA averaged 40 μg/ml and peaked at approximately 4 hr following dosing then decreased to just above basal levels by 24 hr post dosing.

The effect of the formulations 2a to 2f on the bioavailability of omega-3 in the blood of SD rats was examined over a 24 hour treatment period.

Figure 2:
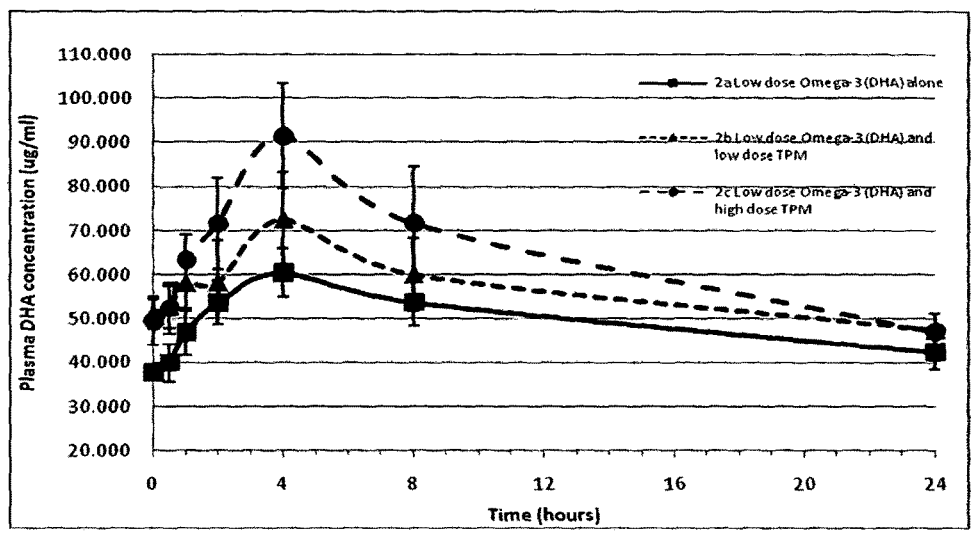
FIG. 2 is a graph showing the plasma omega-3 concentration (ng/ml) measured in rats treated with nutraceutical compositions over a 24 hour period.

Over the 24 hour period examined the omega-3 (DHA) concentration appeared to follow a dose-dependant relationship increasing with the increase in the amount of non-neutralised α-tocopheryl phosphate content or higher non-neutralised α-tocopheryl phosphate ratio compared to the omega-3 (DHA) alone dose, as shown in FIG. 2. There are also significant increases in the first 8 hours (peaking at the 4 hr time-point), in the formulations 2b and 2c versus formulation 2a.

Figure 3:
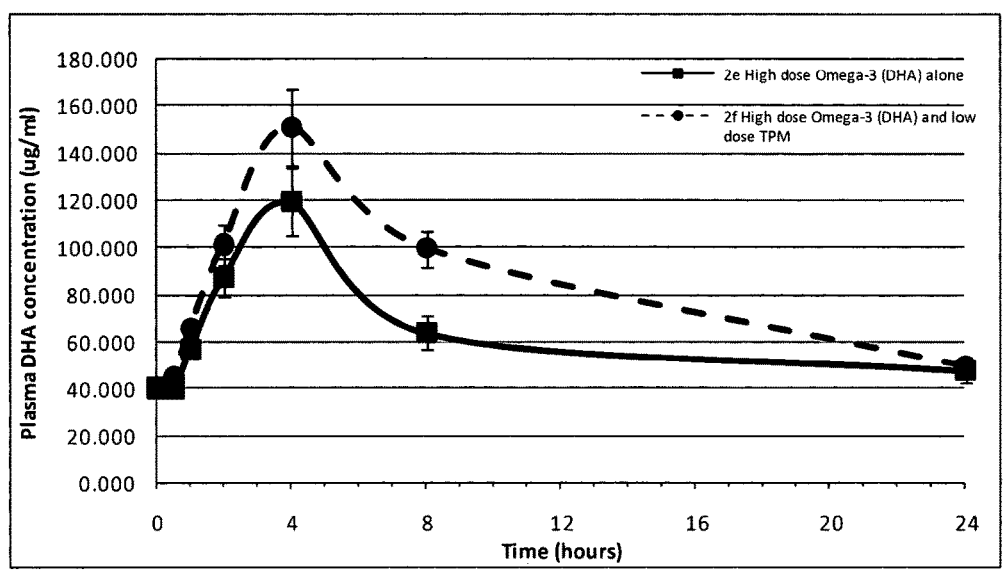
FIG. 3 is a graph showing the plasma omega-3 concentration (ng/ml) measured in rats treated with nutraceutical compositions over a 24 hour period.

FIG. 3 shows that even when a higher dose of omega-3 (DHA) is administered to the rats, formulation 2f showed a significant increase in the level of DHA detected in the blood over the first 24 hours following a single dose (particularly between 4-8 hr time-points).

Figure 4:
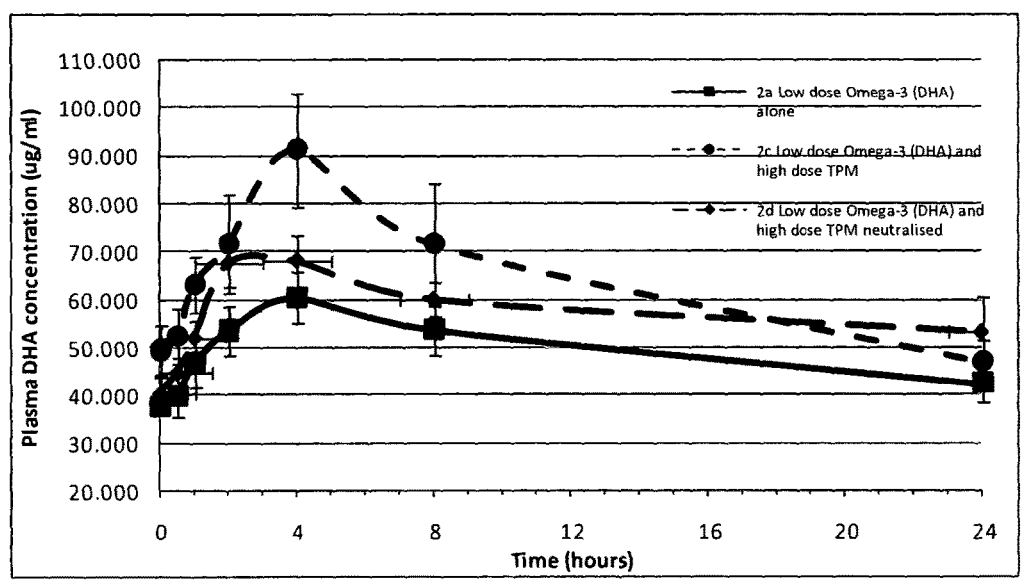
FIG. 4 is a graph showing the plasma omega-3 concentration (ng/ml) measured in rats treated with nutraceutical compositions over a 24 hour period.

FIG. 4 shows the difference between formulations 2c and 2d, which contain neutralised and purified tocopheryl phosphate (2d) and non-neutralised tocopheryl phosphate (2c). The concentration of omega-3 in formulations 2c and 2d was the same as was the concentration of tocopheryl phosphate used in the final formulations in each case. Although both formulations 2c and 2d appear to be more effective than omega-3 alone, formulation 2c, which contains the non-neutralised tocopheryl phosphate was better at improving the bioavailability of omega-3 in the plasma. The non-neutralised tocopheryl phosphate therefore appears to be significantly more effective than the neutralised and purified tocopheryl phosphate in delivery of the omega-3 and provides improved bioavailability of omega-3 over a 24 hour period.

Conclusion

DHA plasma concentration followed a dose-dependent increase with increasing levels of non-neutralised tocopheryl phosphate. At a low dosage of omega-3 alone (HED 1 g), plasma DHA levels exhibited a 50% increase in peak levels (60 μg/ml) when the rats were dosed with formulation 2b. A 75% increase in peak levels (70 μg/ml) was observed when the rats are dosed with formulation 2c, while an 80% increase in peak levels (90 μg/ml) was observed when the rats are dosed with formulation 2f, compared to baseline levels. Although the neutralised and purified tocopheryl phosphate formulation 2d, increased DHA plasma levels (compared to formulation 2a which contained omega-3 alone), the non-neutralised tocopheryl phosphate formulation 2c, was more effective in improving the bioavailability of DHA. At the high dose of omega-3 alone (HED 3 g), plasma DHA levels increased 200% (120 μg/ml) by 4 hr post dosing with formulation 2e, whilst adding non-neutralised tocopheryl phosphate to the formulation (formulation 2f) increased DHA levels to 275% (150 μg/ml).

Thus, co-administering omega-3 and non-neutralised tocopheryl phosphate significantly increased bioavailability of DHA in the plasma.

Example 3: Formulation of Sodium Selenite

A supplement of the following formulation was prepared:

| Amount | Component |
|---|---|
| 1% WW (1-2%) | Non neutralised α-tocopheryl phosphate mixture (prepared as in example 1) |
| 0.1% w/w (0.1-0.2%) | β carotene |
| 0.02% w/w | Sodium Selenite |
| To 100% | Olive Oil |

The formulation was prepared by combining the TPM with the oil first with stirring, at about 70 degrees Celsius. The mixture was then cooled to below 40 degrees Celsius and the beta-carotene added, with stirring, followed by addition of the sodium selenite.

The formulation was a light to dark orange/brown liquid (depending on amount of β carotene used) with no visible particulate matter or aqueous phase.

Many modifications may be made to the embodiments and examples described above without departing from the spirit and scope of the invention.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A carrier for the delivery of a nutraceutical or cosmeceutical active comprising non-neutralised tocopheryl phosphate and a hydrophobic vehicle, wherein the non-neutralised tocopheryl phosphate comprises a mixture of mono-(tocopheryl) phosphate and di-(tocopheryl) phosphate, and wherein the pH of the non-neutralised tocopheryl phosphate is in a range of about 2 to about 4, and wherein the carrier comprises the hydrophobic vehicle in an amount of at least about 80.0% w/w of the total concentration of the carrier.

2. The carrier of claim 1, wherein the pH of the non-neutralised tocopheryl phosphate is about 2 or 3.

3. The carrier of claim 1, wherein the mixture of mono-(tocopheryl) phosphate and di-(tocopheryl) phosphate comprises: (a) a compound selected from the group consisting of mono-(tocopheryl) phosphate, mono-(tocopheryl) phosphate monosodium salt, mono-(tocopheryl) phosphate disodium salt, and a mixture thereof; and (b) a compound selected from the group consisting of di-(tocopheryl) phosphate, di-(tocopheryl) phosphate monosodium salt, and a mixture thereof.

4. The carrier of claim 1, wherein the mono-(tocopheryl) phosphate and di-(tocopheryl) phosphate are present in the mixture in a ratio of at least 2:1.

5. The carrier of claim 1, wherein the hydrophobic vehicle is an oil or a wax.

6. The carrier of claim 5, wherein the hydrophobic vehicle is an edible oil, a vegetable oil, a fruit oil, a seed oil, a grain oil, a nut oil or a polyunsaturated oil containing polyunsaturated fatty acids, an essential or therapeutically-active oil, a silicone oil, or an organic liquid.

7. The carrier of claim 5, wherein the hydrophobic vehicle is beeswax.

8. A formulation comprising the carrier of claim 1 and a nutraceutical or cosmeceutical active.

9. The formulation of claim 8, wherein the formulation is for topical, enteral or parenteral administration.

10. The formulation of claim 9, wherein the formulation is for epicutaneous, oral or transdermal administration.

11. The formulation of claim 8, wherein the nutraceutical and/or cosmeceutical active is selected from the group consisting of vitamins, minerals, amino acids, herbs or other botanicals, enzymes, prebiotics, ubiquinone, ubiquinol, omega-3 fatty acids, lycopene, resveratrol, vitamin E, vitamin D, β-carotene, lutein, zeaxanthin and sodium selenite.

12. The carrier of claim 1, wherein the mono-(tocopheryl) phosphate and di-(tocopheryl) phosphate are present in the mixture in a ratio within a range of about 4:1 to about 1:4.

13. The carrier of claim 1, wherein the mono-(tocopheryl) phosphate and di-(tocopheryl) phosphate are present in the mixture in a ratio within a range of about 6:4 to about 8:2.

14. The carrier of claim 1, wherein the carrier comprises the non-neutralised tocopheryl phosphate in an amount from about 0.1% w/w up to about 5% w/w of the total concentration of the carrier.

15. The carrier of claim 1, wherein the carrier comprises the non-neutralised tocopheryl phosphate in an amount from about 0.01% w/w up to about 5% w/w of the total concentration of the carrier.

16. The carrier of claim 1, wherein the carrier comprises the hydrophobic vehicle in an amount of at least about 90.5% w/w of the total concentration of the carrier.

17. The carrier of claim 1, wherein the carrier comprises the hydrophobic vehicle in an amount of at least about 99.0% w/w, of the total concentration of the carrier.

18. The carrier of claim 5, wherein the hydrophobic vehicle is an oil selected from vegetable oils, fruit oils, seed oils, grain oils, and nut oils.

* * * * *